US007771977B2

(12) United States Patent
Onodera et al.

(10) Patent No.: US 7,771,977 B2
(45) Date of Patent: Aug. 10, 2010

(54) ALKANE POLYOL DEHYDROGENASE

(75) Inventors: Keiko Onodera, Ikoma (JP); Yoshiki Tani, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 0 days.

(21) Appl. No.: 12/311,326

(22) PCT Filed: Apr. 13, 2007

(86) PCT No.: PCT/JP2007/058203

§ 371 (c)(1),
(2), (4) Date: May 11, 2009

(87) PCT Pub. No.: WO2008/041385

PCT Pub. Date: Apr. 10, 2008

(65) Prior Publication Data

US 2009/0263862 A1 Oct. 22, 2009

(30) Foreign Application Priority Data

Sep. 29, 2006 (JP) .............................. 2006-268794

(51) Int. Cl.
C12P 7/26 (2006.01)
C12P 7/02 (2006.01)
C12N 9/02 (2006.01)
C12N 1/20 (2006.01)
C07H 21/04 (2006.01)

(52) U.S. Cl. ....................... 435/148; 435/155; 435/189; 435/252.33; 435/320.1; 536/23.2; 536/23.1

(58) Field of Classification Search ....................... None
See application file for complete search history.

(56) References Cited

U.S. PATENT DOCUMENTS

| 6,818,426 | B2 | 11/2004 | Yamamoto et al. |
| 2003/0032153 | A1 | 2/2003 | Yamamoto et al. |

FOREIGN PATENT DOCUMENTS

| EP | 0 537 456 | 4/1993 |
| JP | 57-183799 | 11/1982 |
| JP | 5-284973 | 11/1993 |
| JP | 8-173170 | 7/1996 |
| JP | 2000-189170 | 7/2000 |
| JP | 2002-125686 | 5/2002 |
| JP | 2002-345479 | 12/2002 |
| JP | 2005-218349 | 8/2005 |

OTHER PUBLICATIONS

Yamada-Onodera et al. "Purification and characterization of an enzyme that has dihydoxyaceton-reducing activity . . . " J. Biosci. Bioengin. 1999, 88 (2), 148-152.*

Database DDBJ/EMBL/GenBank [Online], Accession No. AB257138, (Apr. 14, 2006 uploaded), K. Yamada-Onodera et al., Definition: *Pichia ofunaensis* glydh gene for glycerol dehydrogenase, complete cds., (retrieved on Jun. 11, 2007).

K. Yamada-Onodera et al., "Characterisation of Glycerol Dehydrogenase from a Methylotrophic Yeast, *Hansenula polymorpha* D1-1, and its Gene Cloning", Acta Biotechnol., vol. 22, No. 3-4, pp. 337-353, 2002.

K. Yamada-Onodera et al., "Expression of the Gene of Glycerol Dehydrogenase from *Hansenula polymorpha* D1-1 in *Escherichia coli* for the Production of Chiral Compounds", Acta Biotechnol., vol. 22, No. 3-4, pp. 355-362, 2002.

K. Yamada-Onodera et al., "Purification, Characterization, and Gene Cloning of Glycerol Dehydrogenase from *Hansenula ofunaensis*, and its Expression for Production of Optically Active Diol", Journal of Bioscience and Bioengineering, vol. 102, No. 6, pp. 545-551, Dec. 2006.

M. J. Zoller et al., "Oligonucleotide-directed mutagenesis using M13-derived vectors: an efficient and general procedure for the production of point mutations in any fragment of DNA", Nucleic Acids Research, vol. 10, No. 20, pp. 6487-6500, 1982.

A. Diamond et al., "Methods of RNA Sequence Analysis", Methods in Enzymology, vol. 100, pp. 431-453, 1983.

S. F. Altschul et al., "Basic Local Alignment Search Tool", J. Mol. Biol., vol. 215, pp. 403-410, 1990.

M. Hunkapiller et al., "A microchemical facility for the analysis and synthesis of genes and proteins", Nature, vol. 310, pp. 105-111, Jul. 12, 1984.

J. Reiser et al., "Transfer and Expression of Heterologous Genes in Yeasts Other than *Saccharomyces cerevisiae*", Advances in Biochemical Engineering/Biotechnology, vol. 43, pp. 75-102, 1990.

M. A. Romanos et al., "Foreign Gene Expression in Yeast: a Review", Yeast, vol. 8, pp. 423-488, 1992.

K. Miwa et al., "Construction of novel shuttle vectors and a cosmid vector for the glutamic acid-producing bacteria *Brevibacterium lactofermentum* and *Corynebacterium glutamicum*", Gene, vol. 39, pp. 281-286, 1985.

(Continued)

*Primary Examiner*—Nashaat T Nashed
(74) *Attorney, Agent, or Firm*—Wenderoth, Lind & Ponack, L.L.P.

(57) ABSTRACT

Disclosed is a protein selected from:
(1) a protein comprising the amino acid sequence of SEQ ID NO: 1 in the Sequence Listing;
(2) a protein comprising the amino acid sequence of SEQ ID NO: 1 in the Sequence Listing with the deletion, addition, insertion and/or substitution of one or more amino acid residues, and having an alkane polyol dehydrogenase activity; or
(3) a protein comprising an amino acid sequence having 80% or more identity with the amino acid sequence of SEQ ID NO: 1 in the Sequence Listing, and having an alkane polyol dehydrogenase activity.

Also disclosed is a process for producing an alcohol, a ketone, an optically-active alcohol, dihydroxyacetone or a derivative thereof, using the protein.

9 Claims, 1 Drawing Sheet

OTHER PUBLICATIONS

A. Ozaki et al., "Functional expression of the genes of *Escherichia coli* in gram-positive *Corynebacterium glutamicum*", Mol. Gen. Genet, vol. 196, pp. 175-178, 1984.

D. Simon et al., "Protoplast transformation of group N streptococci with cryptic plasmids", FEMS Microbiology Letters, vol. 26, pp. 239-241, 1985.

J. Kok et al., "Cloning and Expression of a *Streptococcus cremoris* Proteinase in *Bacillus subtilis* and *Streptococcus lactis*", Applied and Environmental Microbiology, vol. 50, No. 1, pp. 94-101, Jul. 1985.

E. M. Gibson et al., "Transfer of Plasmid-Mediated Antibiotic Resistance from *Streptococci* to *Lactobacilli*", Journal of Bacteriology, vol. 137, No. 1, pp. 614-619, Jan. 1979.

Y. Hashimoto et al., "Development of a host-vector system in a *Rhodococcus* strain and its use for expression of the cloned nitrile hydratase gene cluster", Journal of General Microbiology, vol. 138, pp. 1003-1010, 1992.

J. M. Ward et al., "Construction and characterisation of a series of multi-copy promoter-probe plasmid vectors for *Streptomyces* using the aminoglycoside phosphotransferase gene from Tn5 as indicator", Mol. Gen. Genet, vol. 203, pp. 468-478, 1986.

S. Kuhstoss et al., "A thiostrepton-inducible expression vector use in *Streptomyces* spp.", Gene, vol. 103, pp. 97-99, 1991.

U. F. Wehmeier., "New multifunctional *Escherichia coli-Streptomyces* shuttle vectors allowing blue-white screening on XGal plates", Gene, vol. 165, pp. 149-150, 1995.

R. Kawachi et al., "Development of a Transformation System in *Streptomyces virginiae*", Actinomycetol., vol. 11, No. 2, pp. 46-53, 1997.

N. Gunge et al., "Isolation and Characterization of Linear Deoxyribonucleic Acid Plasmids from *Kluyveromyces lactis* and the Plasmid-Associated Killer Character", Journal of Bacteriology, vol. 145, No. 1, pp. 382-390, Jan. 1981.

W. Heyer et al., "Replicating Plasmids in *Schizosaccharomyces pombe*: Improvement of Symmetric Segregation by a New Genetic Element", Molecular and Cellular Biology, vol. 6, No. 1, pp. 80-89, Jan. 1986.

M. McLeod et al., "The product of the mei3$^+$ gene, expressed under control of the mating-type locus, induces meiosis and sporulation in fission yeast", The EMBO Journal, vol. 6, No. 3, pp. 729-736, 1987.

A. Toh-e et al., "Physical and functional structure of a yeast plasmid, pSB3, isolated from *Zygosaccharomyces bisporus*", Nucleic Acids Research, vol. 13, No. 12, pp. 4267-4283, 1985.

Y. Ogawa et al., "Secretion of *Aspergillus oryzae* Alkaline Protease in an Osmophilic Yeast, *Zygosaccharomyces rouxii*", Agric. Biol. Chem., vol. 54, No. 10, pp. 2521-2529, 1990.

Z. A. Janowicz et al., "Simultaneous Expression of the S and L Surface Antigens of Hepatitis B, and Formation of Mixed Particles in the Methylotrophic Yeast, *Hansenula polymorpha*", Yeast, vol. 7, pp. 431-443, 1991.

J. M. Cregg et al., "*Pichia pastoris* as a Host System for Transformations", Molecular and Cellular Biology, vol. 5, No. 12, pp. 3376-3385, Dec. 1985.

J. F. Tschopp et al., "Expression of the *lacZ* gene from two methanol-regulated promoters in *Pichia pastoris*" Nucleic Acids Research, vol. 15, No. 9, pp. 3859-3876, 1987.

S. Kawai et al., "Subcloning and Nucleotide Sequencing of an ARS Site of *Candida maltosa* Which Also Functions in *Saccharomyces cerevisiae*", Agric. Biol. Chem., vol. 51, pp. 1587-1591, 1987.

G. Saunders et al., "Heterologous gene expression in filamentous fungi", Trends in Biotechnology, vol. 7, pp. 283-287, Oct. 1989.

D. R. Cryer et al., "Isolation of Yeast DNA", Meth. Cell Biol., vol. 12, pp. 39-44, 1975.

J. A. Harkki et al., "A Novel Fungal Expression System: Secretion of Active Calf Chymosin from the Filamentous Fungus *Trichoderma Reesi*", Bio/Technology, vol. 7, pp. 596-603, Jun. 1989, excluding pp. 601-602.

\* cited by examiner

ALKANE POLYOL DEHYDROGENASE

This application is a U.S. national stage of International Application No. PCT/JP2007/058203, filed Apr. 13, 2007.

TECHNICAL FIELD

The present invention mainly relates to a novel alkane polyol dehydrogenase and usage thereof.

BACKGROUND ART

Chiral compounds have variable isomers with different bioactivities. Therefore, there has been a constant need for the analysis, development, and production of chiral compounds, particularly in the medical field, agricultural chemistry field, etc.

Typical chiral compound production uses an optically active synthetic unit as a starting material, and the optically active synthetic unit is converted into the target substance. Among various chiral compounds, optically active alcohols are attracting attention as particularly useful compounds.

In the production of optically active alcohols, a method using microorganisms or enzymes has shown promise due to its advantageously high stereospecificity and temperate reaction conditions. In the past, there were some reports of optically active alcohol production methods using highly stereospecific enzymes.

For example, Patent Document 1 discloses a method for producing (R)-2,3-butanediol from (R)-2,3-butanediol dehydrogenase derived from *Pichia angusta*.

Further, Patent Document 2 discloses a method for producing (R)-1,3-butanediol from R-specific alcohol dehydrogenase derived from *Pichia ofunaensis*.

Patent Document 1: Japanese Unexamined Patent Publication No. 2002-125686
Patent Document 2: Japanese Unexamined Patent Publication No. 2005-218349

DISCLOSURE OF INVENTION

Technical Problem

A major object of the present invention is to provide a novel alkane polyol dehydrogenase and usage thereof.

One of the objects of the present invention is to provide a method for producing an optically active alcohol using the dehydrogenase.

Another object of the present invention is to provide a method for producing a ketone using the dehydrogenase.

Still another object of the present invention is to provide a method for producing a useful material from glycerol, using the dehydrogenase.

TECHNICAL SOLUTION

In order mainly to attain the foregoing objects, the inventors of the present invention conducted intensive studies regarding the protein having an activity with respect to alkane polyol.

As a result, the inventors found that a protein derived from *Pichia ofunaensis* (formerly known as *Hansenula ofunaensis*) has an excellent activity with respect to alkane polyol. The inventors conducted further research based on this finding and completed the present invention.

Specifically, the present invention relates to the following proteins, nucleotides, transformant, and production processes.

Item 1. A protein selected from:
(1) a protein comprising the amino acid sequence of SEQ ID NO: 1 in the Sequence Listing;
(2) a protein comprising the amino acid sequence of SEQ ID NO: 1 in the Sequence Listing with the deletion, addition, insertion and/or substitution of one or more amino acid residues, and having an alkane polyol dehydrogenase activity; or
(3) a protein comprising an amino acid sequence having 80% or more identity with the amino acid sequence of SEQ ID NO: 1 in the Sequence Listing, and having an alkane polyol dehydrogenase activity.

The protein according to Item 1, wherein the protein is preferably alkane polyol dehydrogenase.

The protein according to Item 1, wherein the protein is preferably long-chain alkane polyol dehydrogenase, or glycerol dehydrogenase.

The protein according to Item 1, wherein the alkane polyol dehydrogenase activity is preferably a dehydrogenase activity with respect to an alkane polyol having five or more carbon atoms.

The protein according to Item 1, wherein the alkane polyol dehydrogenase activity is preferably a dehydrogenase activity with respect to an alkane polyol having adjacent hydroxyl groups.

Item 2: A polynucleotide selected from:
(a) a polynucleotide having a base sequence that encodes a protein comprising the amino acid sequence of SEQ ID NO: 1 in the Sequence Listing;
(b) a polynucleotide having a base sequence that encodes a protein comprising the amino acid sequence of SEQ ID NO: 1 in the Sequence Listing with the deletion, addition, insertion and/or substitution of one or more amino acid residues, and having an alkane polyol dehydrogenase activity;
(c) a polynucleotide having a base sequence that encodes a protein comprising an amino acid sequence having 80% or more identity with the amino acid sequence of SEQ ID NO: 1 in the Sequence Listing, and having an alkane polyol dehydrogenase activity;
(d) a polynucleotide having a base sequence of SEQ ID NO: 2 in the Sequence Listing; or
(e) a polynucleotide having a base sequence that hybridizes under stringent conditions with a base sequence of SEQ ID NO 2, and that encodes a protein having an alkane polyol dehydrogenase activity.

The polynucleotide according to Item 1, wherein the alkane polyol dehydrogenase activity is preferably a dehydrogenase activity with respect to an alkane polyol having five or more carbon atoms.

Item 3: A transformant containing a recombinant vector containing the polynucleotide according to Item 2.

Item 4: A process for producing the protein according to Item 1, comprising the steps of:
culturing the transformant of Item 3; and
collecting an expression product.

Item 5: A process for producing alcohol, comprising the step of causing the protein of Item 1 to act on a ketone.

The process according to Item 5, preferably comprising the steps of:
reducing the protein of Item 1 by causing it to act on a ketone; and
isolating the produced alcohol.

The process according to Item 5, preferably comprising the steps of:
reducing the protein of Item 1 by causing it to act on a polyketone having five or more carbon atoms; and
isolating the produced alcohol.

Item 6: A process for producing a ketone, comprising the step of causing the protein of Item 1 to act on alcohol.

The process according to Item 6, preferably comprising the steps of:
oxidizing the protein of Item 1 by causing it to act on an alkane polyol; and
isolating the produced ketone.

Item 7: A process for producing an optically active alcohol, comprising the step of causing the protein of Item 1 to act on a prochiral ketone.

The process according to Item 7, preferably comprising the steps of:
reducing the protein of Item 1 by causing it to act on the prochiral ketone; and
isolating the produced optically active alcohol.

Item 8: A process for producing an optically active alcohol, comprising the steps of causing the protein of Item 1 to act on racemic alcohol, and isolating a ketone body product.

The process according to Item 8, preferably comprising the steps of:
causing the protein of Item 1 to act on racemic alcohol to oxidize alcohol having a hydroxyl group in the R configuration; and
isolating the produced ketone.

The process according to Item 8, preferably comprising the steps of:
causing the protein of Item 1 to act on racemic alcohol to oxidize alcohol having a hydroxyl group in the R configuration; and
isolating the produced optically active alcohol having a hydroxyl group in the S configuration.

Item 9: A process for producing dihydroxyacetone or a derivative thereof, comprising the step of causing the protein of Item 1 to act on glycerol.

The process according to Item 9, preferably comprising the steps of:
oxidizing the protein of Item 1 by causing it to act on glycerol; and
isolating the produced dihydroxyacetone.

Item 10: Use of the protein of Item 1 for reducing a ketone to produce alcohol.

The process according to Item 10, wherein the process preferably reduces a prochiral ketone to produce an optically active alcohol.

The process according to Item 10, wherein the process preferably reduces a polyketone having five or more carbon atoms to produce alcohol.

Item 11: Use of the protein of Item 1 for oxidizing an alkane polyol to produce a ketone.

The use according to Item 11, preferably for oxidizing an alkane polyol having 5 or more carbon atoms to produce ketone.

Item 12: Use of the protein of Item 1 for oxidizing alcohol having a hydroxyl group in the R configuration in racemic alcohol to produce an optically active alcohol.

The use according to Item 12, preferably for the production of alcohol having a hydroxyl group in the S configuration, by oxidizing alcohol having a hydroxyl group in the R configuration in racemic alcohol; and isolating the produced ketone.

Item 13: Use of the protein of Item 1 for oxidizing glycerol to dihydroxyacetone.

The following more specifically describes the present invention.

1. Protein

The present invention provides a protein selected from:
(1) a protein comprising the amino acid sequence of SEQ ID NO: 1 in the Sequence Listing;
(2) a protein comprising the amino acid sequence of SEQ ID NO: 1 in the Sequence Listing with the deletion, addition, insertion and/or substitution of one or more amino acid residues, and having an alkane polyol dehydrogenase activity; and
(3) a protein comprising an amino acid sequence having 80% or more identity with the amino acid sequence of SEQ ID NO: 1 in the Sequence Listing, and having an alkane polyol dehydrogenase activity.

The deletion, addition, insertion or substitution of the amino acid residue(s) in the amino acid sequence of SEQ ID NO: 1 in the Sequence Listing may be performed, for example, based on the base sequence of SEQ ID NO: 2 in the Sequence Listing, using a site-specific mutation-introducing method (Nucleic Acid Res., 10, pp. 6487 (1982), Methods in Enzymol., 100, pp. 448 (1983), Molecular Cloning 2nd Edt., Cold Spring Harbor Laboratory Press (1989), PCR A Practical Approach, IRL Press pp. 200 (1991)) or the like.

Examples of the amino acid sequences having 80% or more identity with the amino acid sequence of SEQ ID NO: 1 in the Sequence Listing include amino acid sequences having at least 80%, preferably 90%, more preferably not less than 95%, particularly preferably not less than 99% identity with the amino acid sequence of SEQ ID NO: 1 in the Sequence Listing.

In the present specification, "80% or more identity" is determined, for example, by referring to the value calculated by the BLAST program (J. Mol. Biol., 215, 403-410 (1990)).

The search regarding the amino acid sequence identity may be performed, for example, using a BLAST program, a FASTA program etc. with data bases such as SWISS-PROT, PIR, or DAD that include protein amino acid sequences; data bases such as DDBJ, EMBL, or Gene-Bank (NCBI) that include DNA sequences; and data bases regarding prospective amino acid sequences based on DNA sequences.

"Alkane polyol dehydrogenase activity" is defined by at least the following characteristics (i) and (ii).

(i) Function:
1) a property to reduce a ketone using a reduced β-nicotin amide adenine dinucleotide as a coenzyme to produce a corresponding alcohol.
2) a property to oxidize an alcohol using an oxidized β-nicotin amide adenine dinucleotide as a coenzyme to produce a corresponding ketone.

(ii) Substrate Specificity:
1) a property to cause oxidization using an oxidized β-nicotin amide adenine dinucleotide as a coenzyme.
2) a property to cause reduction using a reduced β-nicotin amide adenine dinucleotide as a coenzyme.
a property to specifically oxidize alkane polyol having two or more adjacent hydroxyl groups so as to produce a corresponding ketone.

"Alkane polyol dehydrogenase activity" may also have the following characteristics.

a property of preferentially oxidizing the R-configuration hydroxyl group of a long-chain alkane polyol so as to produce a corresponding ketone (e.g., preferentially oxidizing the R-configuration hydroxyl group of 1,2-octanediol to produce 1-hydroxy-2-octanone).

a property of preferentially reducing ketone having two or more adjacent carbonyl groups to produce a corresponding alcohol (e.g., preferentially reducing a long-chain ketone having two or more adjacent carbonyl groups, such as 2,3-pentanedione, 2,3-hexanedione or 3,4-hexanedione, to produce a corresponding alcohol).

Such functions and substrate specificities of the present invention can be confirmed using the following measurement methods.

Reduction Activity

The reaction solutions were prepared using plural substrates with varied concentrations. Each solution contained a substrate, 0.2 mM NADH, and an enzyme, and was allowed to react in a 100 mM potassium phosphate buffer solution (pH 6.0) at 25° C. Then, changes in absorbance (molar absorption coefficient 6,220 $M^{-1} \cdot cm^{-1}$) at 340 nm due to the NADH reduction were measured. 1 U is defined as an enzyme amount for catalyzing 1 μmol NADH reduction per minutes.

Oxidization Activity

The reaction solutions were prepared using plural substrates with varied concentrations. Each solution contained a substrate, 2 mM $NAD^+$, and an enzyme, and was allowed to react in a 100 mM potassium phosphate buffer solution (pH 8.0) at 25° C. Then, changes in absorbance (molar absorption coefficient 6,220 $M^{-1} \cdot cm^{-1}$) at 340 nm due to the NADH formation were measured. 1 U is defined as an enzyme amount for catalyzing 1 μmol NADH formation per minute.

By having such characteristics, the protein of the present invention is useful as an alkane polyol dehydrogenase.

Particularly, the protein of the present invention has an excellent dehydrogenase activity with respect to a long-chain alkane polyol such as 1,2-pentanediol, 1,2-hexanediol, 1,2-heptanediol, or 1,2-octanediol.

In the present specification, "long-chain alkane polyol" represents alcohols having five or more, preferably six or more, more preferably seven or more carbon atoms, particularly alcohols having 5 to 100, preferably 5 to 30, more preferably 5 to 20 carbon atoms, and having two or more hydroxyl groups.

By having such characteristics, the protein of the present invention is particularly useful as a long-chain alkane polyol dehydrogenase.

In addition, the protein of the present invention has an excellent oxidization activity (dehydrogenation activity) with respect to an alcohol having a hydroxyl group in each of the adjacent carbon atoms, i.e., an adjacent-alkane diol.

In the present specification, "adjacent-alkane diol" represents alcohols having adjacent carbon atoms, each of which contains a hydroxyl group; in other words, alcohols having adjacent hydroxyl groups. The range of adjacent-alkane diol includes not only alcohols having only two adjacent hydroxyl groups but also alcohols having one or more hydroxyl groups in addition to the adjacent ones. The adjacent-alkane diol may be expressed as an alkane polyol having two adjacent hydroxyl groups.

Examples of adjacent-alkane diols include an alkanol having hydroxyl groups in the carbon atoms at the first and second positions, such as 1,2-pentanediol, 1,2-hexanediol, 1,2-heptanediol or 1,2-octanediol; and an alkanol having hydroxyl groups at the first, second, and fourth positions, such as 1,2,4-butanetriol.

With such characteristics, the protein of the present invention is useful as a dehydrogenase for alcohols having adjacent hydroxyl groups; in other words, as a dehydrogenase for alcohols having an adjacent-alkane diol.

Further, the protein of the present invention has an excellent oxidization activity with respect to glycerol, and is useful as a glycerol dehydrogenase.

Furthermore, the protein of the present invention has an excellent reduction activity with respect to ketones such as dihydroxyacetone, 3-hydroxy-2-butanone, acetol, 2,3-pentanedione, 2,3-hexanedione, or 3,4-hexanedione, particularly to a ketone having five or more, preferably six or more carbon atoms.

The protein of the present invention particularly has an excellent reduction activity with respect to ketones having adjacent carbonyl groups, such as 2,3-pentanedione, 2,3-hexanedione, or 3,4-hexanedion.

The protein of the present invention has more significant reduction activity with respect to long-chain ketones. In the present specification, "long-chain ketone" represents a ketone having five or more, preferably six or more, more preferably seven or more carbon atoms, and particularly a ketone having 5 to 100, preferably 5 to 30, more preferably 5 to 20 carbon atoms.

The protein of the present invention has specificity with respect to R-configuration hydroxyl groups. The specificity is particularly high with respect to the R-configuration hydroxyl groups in long-chain alkane polyols.

For example, when causing the protein of the present invention to act on a (R,S)-long-chain adjacent-alkane diol, only the (R)-long-chain adjacent-alkane diol is selectively oxidized. By isolating the ketone resulting from the oxidization, it is possible to obtain only the (S)-long-chain adjacent-alkane diol having high optical purity.

Molecular Weight

The molecular weight of the protein of the present invention can be measured using a general technique, such as SDS-PAGE, gel filtration chromatography or the like.

For example, for the protein having the amino acid sequence of SEQ ID NO: 1 in the Sequence Listing, the molecular weight of the subunits, which is measured by SDS-PAGE (dodecyl sodium sulfate-polyacrylamide gel electrophoresis), is about 39,000.

According to the measurement using gel filtration chromatography, the molecular weight of the protein having the amino acid sequence of SEQ ID NO: 1 in the Sequence Listing is about 58,000.

Process for Producing Protein

Examples of proteins having such a property include proteins derived from methanol metabolizing enzyme *Pichia ofunaensis* (formerly known as *Hansenula ofunaensis*).

Examples of *Pichia ofunaensis* include *Pichia ofunaensis* CBS8129, and *Pichia ofunaensis* AKU4328.

*Pichia ofunaensis* is a kind of strain originally isolated to serve as a methanol metabolizing enzyme. *Pichia ofunaensis* was first called *Hansenula ofunaensis* as a novel strain, then was reclassified and given the new name *Pichia ofunaensis*. After the filing of the basic application of the present invention, this microorganism was further reclassified, and its name was changed again from "*Pichia ofunaensis*" to "*Zygoascus ofunaensis*". However, the present specification calls the strain by its name at the time of the basic application.

The microorganism is cultured in a general yeast cultivation medium, such as a YM medium (glucose 10 g/L, peptone 5 g/L, yeast extract 3 g/L, malt extract 3 g/L, pH 6.0).

The production of the protein of the present invention using the microorganism can be derived from glycerol serving as a carbon source. For example, the production amount of the protein of the present invention increases by adopting the following method. The preculture is performed in a culture medium prepared by adding 1% glucose to a basal medium A (ammonium chloride 5 g/L, monopotassium dihydrogen phosphate 1 g/L, potassium dihydrogen phosphate 1 g/L, magnesium sulfate heptahydrate 0.5 g/L, iron (III) chloride hexahydrate 30 mg/L, calcium chloride dihydrate 10 mg/L, manganese (II) sulfate pentahydrate 10 mg/L, zinc sulfate heptahydrate 10 mg/L, thiamine hydrochloride 2 mg/L and biotin 20 µg/L), followed by the main culture in an induction culture medium prepared by adding 1% glycerol to a basal medium. The production of the protein of the present invention is thus appropriately performed in a medium containing glycerol.

After sufficient proliferation, the cultured cells are isolated and pulverized in a buffer solution to obtain a cell extract.

The cell extract is then purified by an appropriate combination of: a fraction method (sedimentation using an organic solvent, salt precipitation using an ammonium sulfate, etc.) based on the protein solubility, cation exchange, anion exchange, gel filtration, hydrophobic chromatography, and affinity chromatography using a chelate, colorants, antibody, etc.

For example, the cell extract is purified electrophoretically into a single band through DEAE-cellulose anion-exchange chromatography, a 40% ammonium sulfate fraction method, butyl-Toyopearl hydrophobic chromatography, Superdex 200 gel filtration chromatography or the like, thereby obtaining a purified protein.

The protein of the present invention can also be obtained as follows. The amino acid sequence of the purified protein is assayed, the gene is cloned using a primer created based on the assayed sequence, and then the target protein is obtained using a transformant.

For example, using the purified enzyme thus obtained, the N-terminus amino acid sequence and, by way of partial digestion with a V8 protease, a part of the internal sequence are assayed. Then, a PCR primer is synthesized using the assayed amino acid sequence; PCR is performed using *Pichia ofunaensis*-derived chromosome DNA as a template; the core region is, amplified; and the base sequence of the core region is assayed to obtain a core sequence. Then, the base sequences in the vicinity of 5'- and 3'-terminuses in the core sequence are assayed after the chromosome DNA is digested by a restriction enzyme. More specifically, the base sequences in the vicinity of 5'- and 3'-terminuses are determined using a general PCR technique for cloning the vicinity of 5'- and 3'-terminuses usually adopted by a skilled artisan in the field, for example, according to TAKARA LA PCR in vitro Cloning Kit (Takara Bio Inc.). More specifically, a fragment prepared by digesting the chromosome DNA by a restriction enzyme is connected to a primer cassette containing a cut-end of the restriction enzyme to create a template, and PCR is preformed using a primer created based on a base sequence contained in the core region and a primer having the sequence in the primer cassette (and another PCR using more internal primer set, if necessary). The obtained fragment is assayed to determine the base sequences of 5'- and/or 3'-terminuses. The obtained sequences and the sequence in the core region are assembled to determine the entire base sequence of the enzyme. Based on the base sequence thus determined, a primer capable of specifically amplifying an enzyme open reading frame (ORF) is synthesized, and inserted in an expression vector pSE420D (see Japanese Unexamined Patent Publication No. 2000-189170) in *Escherichia coli* to form an expression plasmid pSE-HOG. The expression plasmid is introduced in *Escherichia coli*, and the resulting transformant is cultured in a suitable culture medium. Finally, the expression product is isolated to obtain the protein of the present invention.

The protein of the present invention can also be produced in the following manner. A suitable primer is created based on the amino acid sequence of SEQ ID NO: 1 in the Sequence Listing, the gene is cloned with the primer, and the target protein is produced using a transformant.

Further, the protein of the present invention can also be obtained by general chemical synthesis of a part or all of the amino acid sequence of SEQ ID NO: 1 in the Sequence Listing, using a peptide synthesizer or the like.

2. Polynucleotide

The present invention provides a polynucleotide selected from:

(a) a polynucleotide comprising a base sequence that encodes a protein comprising the amino acid sequence of SEQ ID NO: 1 in the Sequence Listing;

(b) a polynucleotide comprising the amino acid sequence of SEQ ID NO: 1 in the Sequence Listing with the deletion, addition, insertion and/or substitution of one or more amino acid residues, and having an alkane polyol dehydrogenase activity; and (c) a polynucleotide having a base sequence that encodes a protein comprising an amino acid sequence having 80% or more identity with the amino acid sequence of SEQ ID NO: 1 in the Sequence Listing, and having an alkane polyol dehydrogenase activity;

(d) a polynucleotide having a base sequence of SEQ ID NO: 2 in the Sequence Listing;

(e) a polynucleotide having a base sequence that hybridizes under stringent conditions with a base sequence of SEQ ID NO: 2, and that encodes a protein having an alkane polyol dehydrogenase activity.

The "polynucleotide that hybridizes under stringent conditions" denotes a polynucleotide that undergoes hybridization when using a prove DNA formed of one or more sequences selected from at least 20, preferably at least 30, for example, 40, 60, or 100 continuous sequences in SEQ ID NO: 2, using, for example, an ECL direct nucleic acid labeling and detection system (Anersham Biosciences), under the conditions specified in the manual (e.g., washing: 42° C., primary wash buffer containing 0.5×SSC).

More specifically, the "stringent condition" generally denotes, but is not limited to, a condition of 42° C., 2×SSC, and 0.1% SDS; preferably 50° C., 2×SSC, and 0.1% SDS; further preferably 65° C., 0.1×SSC, and 0.1% SDS. Several factors including temperature, salt concentration etc. may influence the stringency in the hybridization, and the optimum stringency can be set by appropriate settings of these factors according to a skilled artisan.

The polynucleotide of the present invention may be a natural polynucleotide such as DNA, RNA etc., or an artificial molecule containing an artificial nucleotide derivative, or a DNA/RNA chimeric molecule.

Examples of the polynucleotides of the present invention include polynucleotides derived from *Pichia ofunaensis*. Examples of *Pichia ofunaensis* include *Pichia ofunaensis* CBS8129 and *Pichia ofunaensis* AKU4328.

As mentioned above, *Pichia ofunaensis* was reclassified after the filing of the basic application of the present invention. The sequences of SEQ ID NO: 1 and SEQ ID NO: 2 in the Sequence Listing were registered to the DNA Data Bank of Japan (DDBJ) as information of *Pichia ofunaensis*-derived enzyme (Accession Number AB257138), and published in Apr. 14, 2006. After that, the details in GenBank administered by Taxonomy were modified, and the name in the DDBJ was also changed from "organism="*Pichia ofunaensis*" to "/note="synonym: *Pichia ofunaensis*"/organism="*Zygoascus ofunaensis*" in January, 2007.

For example, the polynucleotide of the present invention can be produced as follows. A PCR primer is designed based on the base sequence of SEQ ID NO 2; and PCR is performed using a *Pichia ofunaensis*-derived chromosome DNA or a cDNA library as a template.

Further, the polynucleotide of the present invention can also be obtained by synthesizing a part or all of the base sequence of SEQ ID NO: 2 in the Sequence Listing according to a general method such as the phosphite-triester method (Nature, 310, 105 (1984)), or using a DNA synthesizer or the like.

By introducing the polynucleotide of the present invention into an expression vector, and collecting the expression product using a transformant, stable mass production of the protein of the present invention is ensured.

3. Transformant

The present invention provides a transformant having a recombinant vector containing the aforementioned polynucleotide.

The transformant of the present invention can be obtained by inserting the polynucleotide of the present invention as described in the section 2 above into an expression vector to create a recombinant vector; and incorporating the recombinant vector into an appropriate host.

The types of the expression vector and the host are not limited insofar as the protein coded by the polynucleotide of the present invention can be expressed.

Examples of the hosts include the following microorganisms.

Bacterias for which the host-vector system is established, such as:
Genus *Escherichia*
Genus *Bacillus*
Genus *Pseudomonas*
Genus *Serratia*
Genus *Brevibacterium*
Genus *Corynebacterium*
Genus *Streptococcus*
Genus *Lactobacillus*
Actinomyces for which the host-vector system is established, such as:
Genus *Rhodococcus*
Genus *Streptomyces*.
Yeasts for which the host-vector system is established, such as:
Genus *Saccharomyces*
Genus *Kluyveromyces*
Genus *Schizosaccharomyces*
Genus *Zygosaccharomyces*
Genus *Yarrowia*
Genus *Trichosporon*
Genus *Rhodosporidium*
Genus *Pichia*
Genus *Candida*
Molds for which the host-vector system is established, such as:
Genus *Neurospora*
Genus *Aspergillus*
Genus *Cephalosporium*
Genus *Trichoderma*.

The expression vector can be selected from suitable known vectors, in consideration of matching with the host.

The creation of the vector may be performed using common technology in the field (e.g., Molecular Cloning, Cold Spring Harbor Laboratories, Sambrook et al.).

To express the protein of the present invention in microorganisms or the like, it is necessary to first introduce the DNA into a plasmid vector or a phage vector stable in the microorganism so that the gene information is transcribed/translated. To facilitate this process, an appropriate promoter or terminator can be used. Any promoter or terminator can be used in so far as it is confirmed to exhibit the function in the host macroorganism.

There are some references to find suitable vectors, promoters and terminators, such as "*Biseibutsugaku-kisokouza* (Basic Microbiology Seminar) 8: *Idenshikougaku* (Gene Engineering): Kyoritsu Shuppan Co., Ltd", or "Adv. Biochem. Eng., 43, 75-102 (1990), Yeast, 8, 423-488 (1992)" especially for yeasts.

For example, for genus *Escherichia*, especially for *Escherichia coli* (*Escherichia coli*), a pBR or pUC plasmid can be used as a plasmid vector, and derivatives of lac (β-galactosidase and trp (tryptophan operon)), tac, trc (fusion of lac and trp), λ phage PL, PR etc can be used as a promoter. For the terminator, derivatives from trpA, phage, rrnB ribosomal RNA, etc. can be used.

Among these, a co-expression vector pSE420D (Japanese Unexamined Patent Publication No. 2000-189170) obtained by partially modifying the multi-cloning site of the commercially available vector pSE420 (produced by Invitrogen) is particularly suitable.

For genus *Bacillus*, a pUB110 or pC194 plasmid can be used as a vector, which can be integrated with a chromosome. For the promoter and/or terminator, apr (alkali protease gene), npr (neutral protease gene), amy (α-amylase gene), etc. are suitable.

For genus *Pseudomonas*, several host vector systems have been developed to be used for *Pseudomonas putida*, *Pseudomonas cepacia* (currently known as *Burkholderia cepacia*), etc. For example, wide host area vector (including gene required for autonomous replication derived from RSF1010) pKT240 or the like based on the TOL plasmid involved in the decomposition of toluene compound is suitable. For the promoter and terminator, a lipase (Japanese Unexamined Patent Publication No. 5-284973) gene or the like is suitable.

The plasmid vector pAJ43 (Gene, 39, 281 (1985)) or the like can be used for genus *Brevibacterium*, especially, *Brevibacterium lactofermentum*. For the promoter and terminator, the same promoter and terminator used for *Escherichia coli* can be used.

For genus *Corynebacterium*, particularly *Corynebacterium glutamicum*, a plasmid vector pCS11 (Japanese Unexamined Patent Publication No. 57-183799), a plasmid vector pCB101 (Mol. Gen. Genet., 196, 175 (1984)) or the like can be used.

For genus *Streptococcus*, a plasmid vector pHV1301 (FEMS Microbiol. Lett., 26, 239 (1985), a plasmid vector pGK1 (Appl. Environ. Microbiol., 50, 94 (1985)) or the like can be used.

For genus *Lactobacillus*, a plasmid vector pAM01 (J. Bacteriol., 137, 614 (1979)), which was developed for *Streptococcus* genus, or the like can be used. For the promoter, the same promoter as that for *Escherichia coli* can be used.

For genus *Rhodococcus*, a plasmid vector isolated from *Rhodococcus rhodochrous* (J. Gen. Microbiol., 138, 1003 (1992)) can be used.

The plasmid for genus *Streptomyces* may be created according to "Genetic Manipulation of *Streptomyces*: A Laboratory Manual", Cold Spring Harbor Laboratories (1985), Hopwood et al. Plasmid pIJ486 (Mol. Gen. Genet., 203, 468-478, 1986), plasmid pKC1064 (Gene, 103, 97-99 (1991)), plasmid pUWL-KS (Gene, 165, 149-150 (1995)), etc. are particularly useful for *Streptomyces lividans*. These plasmids are also useful for *Streptomyces virginiae* (Actinomycetol. 11, 46-53 (1997)).

For genus *Saccharomyces*, especially for *Saccharomyces cerevisiae*, the plasmids YRp, YEp, YCp, or YIp can be used. Particularly useful is an integration vector (EP 537456 etc.) using homologous recombination with many copies of ribosome DNA in the chromosome. The integration vector introduces a large number of DNA copies, and ensures stable retention of the gene. For the promoter and terminator, the promoters/terminators derived from ADH (alcoholdehydrogenase), GAPDH (glyceraldehyde 3-phosphate dehydrogenase), PHO (acid phosphatase), GAL (β-galactosidase), PGK (phosphoglycerate kinase), ENO (enolase), etc. are suitable.

For genus *Kluyveromyces*, particularly for *Kluyveromyces lactis*, a *Saccharomyces cerevisiae*-derived 2 μm plasmid, or a plasmid pKD1 (J. Bacteriol., 145, 382-390 (1981)), a plasmid derived from pGK11 involved in the killer activity, a plasmid of the autonomous replication gene KARS in *Kluyveromyces* genus, or a vector plasmid (EP 537456, etc.) that can be integrated with chromosome through homologous recombination with ribosome DNA or the like, can be used. For the promoter and terminator, the promoters/terminators derived from ADH, PGK, etc. are suitable.

For genus *Schizosaccharomyces*, a plasmid of ARS (gene involved in autonomous replication) derived from *Schizosaccharomyces pombe*, or a plasmid vector derived from *Saccharomyces cerevisiae* containing a selective marker for complementing auxotrophy (Mol. Cell. Biol., 6, 80 (1986)) can be used. For the promoter, for example, an ADH promoter derived from *Schizosaccharomyces pombe* can be used (EMBO J., 6, 729 (1987)).

For genus *Zygosaccharomyces*, a plasmid vector pSB3 (Nucleic Acids Res., 13, 4267 (1985)) derived from *Zygosaccharomyces rouxii* or the like can be used. For the promoter, a PHO5 promoter derived from *Saccharomyces cerevisiae*, or a promoter of GAP-Zr (glyceraldehyde 3-phosphate dehydrogenase) derived from *Zygosaccharomyces rouxii* (Agri. Biol. Chem., 54, 2521 (1990)) is suitable.

For genus *Pichia*, a host vector system was developed to be used for *Pichia angusta* (formerly known as *Hansenula polymorpha*). *Pichia angusta*-derived genes (HARS1 and HARS2) involved in autonomous replication are also useful; however, since they are relatively unstable, multi-copy integration of the gene into a chromosome is preferred (Yeast, 7, 431-443 (1991)). For the promoter, FDH (formic dehydrogenase), AOX (alcohol oxidase), etc. inducible by methanol are suitable. In addition, there is a host vector system (Mol. Cell. Biol., 5, 3376 (1985)) for *Pichia pastoris* etc. that adopts a *Pichia*-derived autonomous replication gene (PARS1, PARS2). This system allows for high-concentration culture and the use of a strong promoter, such as methanol-inducible AOX (Nucleic Acids Res. 15, 3859 (1987)).

For genus *Candida*, several host vector systems were developed for *Candida maltosa, Candida albicans, Candida tropicalis, Candida utilis*, etc. Further, there is a host vector system for *Candida maltosa*, which was created by cloning an ARS derived from *Candida maltosa* (Agri. Biol. Chem. 51, 1587 (1987)). For *Candida utilis*, a strong chromosome-integration vector promoter was developed (Japanese Unexamined Patent Publication No. 1996-173170).

Among genus *Aspergillus* fungi, *Aspergillus niger* and *Aspergillus oryzae*, which can be used with plasmids or chromosome-integration, have particularly been studied. For the promoter, promoters derived from an extracellular protease-gene and amylase gene are suitable (Trends in Biotechnology 7, 283-287 (1989)).

For genus *Trichoderma*, host-vector systems using *Trichoderma reesei* were developed, and some promoters including a promoter derived from an extracellular cellulase gene are available (Biotechnology 7, 596-603 (1989)).

Apart from microorganisms, there are various plants and animal systems that can express foreign proteins. For example, a plant cell, an animal cell, etc. can also be used as a host.

As described, the protein of the present invention can be produced by culturing a transformant obtained by transforming with an expression vector, and collecting the expression product.

The collection of the expression products can be performed using known techniques.

For example, when the host secretes protein outside the cell, the cultured medium is centrifuged to collect a culture supernatant, thereby obtaining a crude protein solution.

When the host does not secrete protein outside the cell, the cells were pulverized by ultrasonic disintegration or the like, followed by centrifugation, thereby obtaining a crude protein solution.

Isolation/purification of the protein from the crude protein solution can also be performed using known techniques.

For example, the isolation/purification may be performed by way of salt precipitation using an ammonium sulfate, electrophoresis, affinity chromatography, dialysis, hydrophobic chromatography, or a combination of these methods.

4. Process for Producing Alcohol

The present invention provides a process for causing the protein of the present invention to act on ketone to produce alcohol.

The protein of the present invention, i.e., alkane polyol dehydrogenase, has a high reduction activity with respect to ketone. Accordingly, causing the enzyme of the present invention to act on ketone produces a corresponding alcohol.

Any kind of ketone may be used insofar as the activity of the protein of the present invention can be exhibited; however, the high reduction activity of the protein of the present invention is more intensively exhibited with respect to a long-chain ketone.

The "long-chain ketone" represents a ketone having 5 to 100, particularly 6 to 100, preferably 5 to 30, more preferably 5 to 20 carbon atoms.

The ketone may be substituted with a lower alkyl group, halogen group, nitro group, alkoxy group, hydroxyl group, carbonyl group, amino group or the like.

The enzyme of the present invention exhibits a high reduction activity particularly with respect to ketone having adjacent carbonyl groups. In the present specification, "ketone having adjacent carbonyl groups" denotes a ketone having a carbonyl group in each of the adjacent carbon atoms, i.e., adjacent carbonyl groups, The ketone having adjacent carbonyl groups may also contain one or more carbonyl groups or hydroxyl groups, in addition to the adjacent carbonyl groups.

Examples of ketones having adjacent carbonyl groups include alkanones such as 2,3-pentanedione, 2,3-hexanedione, or 3,4-hexanedion.

Many of the ketones having adjacent carbonyl groups are reduced to an optically active alcohol, i.e., prochiral ketones.

The enzyme of the present invention acts on a prochiral ketone to preferentially produce R-configuration alcohol.

For example, by causing the protein of the present invention to act on a prochiral ketone such as 2,3-pentanedione, 2,3-hexanedione, or 3,4-hexanedione, the corresponding alcohols, i.e., (R)-2,3-pentanediol, (R)-2,3-hexanediol, or (R)-3,4-hexanediol are obtained.

The process of causing the protein of the present invention to act on a ketone is not particularly limited. For example, it is possible to cause an expression product to act on a ketone. More specifically, it is possible to cause a transformant for expressing the protein of the present invention, such as a transformant obtained by transforming with an expression vector containing the polynucleotide of the present invention, to act on a ketone.

The transformant may be any kind insofar as the protein of the present invention can be effectively expressed. Examples of the transformants include a transformant for expressing the protein of SEQ ID NO: 1, such as *Escherichia coli* transformed by pSE-HOG.

The transformant may co-express an enzyme for recovering NADH, for example, glucose dehydrogenase or formic dehydrogenase, with the enzyme of the present invention.

The transformant may be subjected to appropriate treatment. Examples of the processed transformants include microorganisms treated with an organic solvent, such as surfactant or toluene, to change cell membrane permeability; freeze-dried or spray-dried cell bodies; cell-free extracts, half-purified as required, obtained by pulverizing a cell body with enzymes or glass beads; purified enzymes; immobilized enzymes obtained by immobilizing a transformant or enzyme; and immobilized microorganisms.

It is also possible to cause a cell producing the protein of the present invention to act on ketone.

The process for reacting the protein of the present invention is performed either in water, an organic solvent or in a mixed solvent of water and an organic solvent. Examples of the organic solvents include acetic acid ethyl, acetic acid butyl, toluene, chloroform, and n-hexane.

The reaction process may also be performed using immobilized enzymes, membrane reactors or the like.

In the reaction step, the reaction temperature is 5 to 50° C., preferably 5 to 35° C. The pH is generally 4 to 8, preferably 5 to 7.

The substrate concentration is 0.01 to 90%, preferably 0.1 to 30%. The enzyme concentration is generally 0.01 to 10 unit/ml, preferably 0.1 to 5 unit/ml.

The substrate may be added all at once in the beginning of the reaction; however, it is more preferable to add the substrate in a continuous or discontinuous manner to prevent excessive increase of the substrate concentration in the reaction mixture.

As required, the reaction system may contain coenzyme NADH of about 0.1 to 20 mM, preferably about 1 to 10 mM.

The reaction also derives $NAD^+$ from NADH. The $NAD^+$ may be recovered to NADH using the $NAD^+$ reduction ability of the microorganism (C1 compound metabolic pathway of methylotroph, etc).

For example, it is possible to recover NADH using a microorganism, either processed or unprocessed, containing glucose dehydrogenase, alcoholdehydrogenase, formic dehydrogenase, amino acid dehydrogenase, organic acid dehydrogenase (malate dehydrogenase etc.) etc.; or purified or partially-purified enzymes.

These components for the NADH recovery reaction can be added to the reaction system for producing alcohol of the present invention.

However, it may be possible to omit this extra NADH recovery reaction system when the alcohol production is performed using a live microorganism transformed by a recombinant vector containing the polynucleotide of the present invention. More specifically, by selecting a host from the microorganisms having high NADH recovery activities, the reductive reaction using a transformant can be more efficiently performed without using an NADH recovery enzyme.

The expressions of NADH recovery enzyme and the NAD-dependent R-specific alcohol dehydrogenase, and the reductive reaction can be more efficiently performed by introducing NADH recoverable gene such as glucose dehydrogenase, alcoholdehydrogenase, formic dehydrogenase, amino acid dehydrogenase, or organic acid dehydrogenase (malate dehydrogenase etc.) to a host, together with the DNA for encoding the alkane polyol dehydrogenase of the present invention. The introduction of such two or more kinds of genes into the host is performed by a method for introducing two or more genes into a single vector, a method for introducing one or both of the genes into the chromosome, or a method for transforming the host by a recombinant vector obtained by separately introducing plural genes in separate vectors of different replication origins, so as to eliminate the problem of incompatibility.

When introducing two or more kinds of genes into a single vector, it is possible to connect the regions involved in expression control, such as a promoter, terminator, etc. to each gene, or express the genes as operons, such as lactose operon, containing a plurality of cistrons.

Examples of NADH recovery enzymes include glucose dehydrogenases derived from genus *Bacillus*, genus *Pseudomonas*, genus *Thermoplasma* or the like. A preferred enzyme is a recombinant vector incorporating glucose dehydrogenase gene derived from *Bacillus subtilis*. Additionally, formic dehydrogenases derived from genus *Mycobacterium*, such as a recombinant vector incorporating a formic dehydrogenase derived from *Mycobacterium vaccae*, are also useful as the NADH recovery enzyme.

The purification of alcohol can be performed using a common technique; for example, a combination of two or more of: cell body/protein centrifugation, separation by membrane treatment, solvent extraction, distillation, crystallization and the like.

5. Process for Producing Ketone

The present invention provides a process for causing the protein of the present invention to act on alcohol to produce ketone.

Generally, ketone has a high reactivity, and serves as an intermediate of many compounds. Prochiral ketone is useful as a material of optically-active alcohol, but is generally more expensive than racemic alcohol. The process of the present invention allows for the production of prochiral ketones from inexpensive alcohols.

Any alcohol can be used. Examples of suitable alcohols include, but are not limited to, 1,2-propanediol, 1,2-butanediol, and 2,3-butanediol. By causing the protein of the present invention to act on them, acetol, 1-hydroxy-2-butanone and acetoin, respectively, are obtained.

The process of the present invention is particularly useful as a method for preferentially producing ketone from alcohol having an R-configuration hydroxyl group. The process of the present invention is also useful as a method for preferentially producing ketone from alcohol having two or more adjacent hydroxyl groups.

Acting on alcohol, the protein of the present invention dehydrogenates R-configuration alcohol more preferentially than the S-configuration alcohol, and produces a corresponding ketone. By reducing the isolated ketone, it is possible to selectively obtain R-configuration alcohol.

For example, when causing the protein of the present invention to act on racemic alcohol, R-configuration alcohol is dehydrogenated more preferentially than the S-configuration alcohol, and a corresponding ketone is produced. Prochiral ketone can be produced through this process by reducing R-configuration alcohol. Accordingly, the ketone-production process of the present invention may also be useful for prochiral ketone production.

The process of causing the protein of the present invention to act on alcohol is not particularly limited. For example, it is possible to cause an expression product to act on alcohol. More specifically, a transformant for expressing the protein of the present invention, such as a transformant obtained by transforming with a recombinant vector containing the polynucleotide of the present invention, may be caused to act on ketone. Examples of such transformants include a transformant for expressing the protein of SEQ ID NO: 1 such as *Escherichia coli* transformed by pSE-HOG.

The transformant may be any kind insofar as the protein of the present invention can be effectively expressed. The transformant may co-express an enzyme for recovering NAD$^+$, such as lactate dehydrogenase, with the enzyme of the present invention.

The transformant may be subjected to appropriate treatment. Examples of the processed transformants include microorganisms treated with an organic solvent, such as surfactant or toluene, to change cell membrane permeability; freeze-dried or spray-dried cell bodies; cell-free extracts, half-purified as required, obtained by pulverizing a cell body with enzyme or glass beads; purified enzymes; immobilized enzymes obtained by immobilizing a transformant or enzyme; and immobilized microorganisms. It is also possible to causes a cell body producing the protein of the present invention to act on ketone.

The process for reacting the protein of the present invention is performed either in water, an organic solvent or in a mixed solvent of water and an organic solvent. Examples of the organic solvents include acetic acid ethyl, acetic acid butyl, toluene, chloroform, and n-hexane.

The reaction process may also be performed using immobilized enzymes, membrane reactors or the like.

In the reaction step, the reaction temperature is 5 to 50° C., preferably 5 to 35° C.; and the pH is generally 7 to 9, preferably 8 to 9.

The substrate concentration is 0.01 to 90%, preferably 0.1 to 30%. The enzyme concentration is generally 0.01 to 10 unit/ml, preferably 0.1 to 5 unit/ml.

The substrate may be added all at once in the beginning of the reaction; however, it is more preferable to add the substrate in a continuous or discontinuous manner to prevent excessive increase of the substrate concentration in the reaction mixture.

As required, the reaction system may contain coenzyme NAD of about 0.1 to 20 mM, preferably about 1 to 10 mM.

This oxidization reaction also produces NADH, thereby recovering NAD$^+$ due to the function of the microorganism to recover NAD$^+$ from NADH.

It is also possible to recover NAD$^+$ by adding an enzyme having an activity to oxidize NADH to NAD$^+$, such as lactate dehydrogenases, glutamate dehydrogenases, glucose dehydrogenases, NADH dehydrogenases, NADH oxidases or the like; or processed or unprocessed microorganisms containing these enzymes.

Further, by creating a transformant that co-expresses an enzyme for recovering NAD$^+$ from NADH with the enzyme of the present invention, it is possible to efficiently perform a NAD$^+$ recovery reaction and a stereoselective oxidative reaction.

As required, the production method of the present invention may comprise a process for purifying the obtained ketone.

The ketone purification can be performed using a common technique; for example, a combination of two or more of: centrifugation, separation by membrane treatment, solvent extraction, distillation, crystallization and the like.

6. Process for Producing Optically Active Alcohol

The protein of the present invention, i.e., alkane polyol dehydrogenase, has a particularly high oxidization activity with respect to alcohol having adjacent hydroxyl groups. Many alcohols having adjacent hydroxyl groups are optically active alcohols. The protein of the present invention preferentially reacts with the R-configuration hydroxyl group.

Further, the enzyme of the present invention has a particularly high reduction activity with respect to ketones having adjacent carbonyl groups. Many ketones having adjacent carbonyl groups are prochiral ketones, which are reduced to optically-active alcohol. The enzyme of the present invention acts on prochiral ketones to preferentially produce R-configuration alcohol.

Accordingly, the alkane polyol dehydrogenase of the present invention is useful for the production of optically active alcohols.

(6-1). Reduction of Prochiral Ketone

The present invention provides a process for producing optically active alcohol comprising causing the protein of the present invention to act on prochiral ketones.

Examples of prochiral ketones include 2-pentanone, 3-hexanone, 3-hydroxy-2-butanone, acetol, 2,3-pentanedione, 2,3-hexanedione, and 3,4-hexanedione.

The compound expressed by the following General Formula is an example of a prochiral ketone:

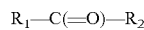

$$R_1-C(=O)-R_2$$

The ketone body may be substituted with lower alkyl group, halogen group, nitro group or alkoxy group. In the present specification, "ketone" may also be referred to as "ketone body".

Among them, the protein of the present invention exhibits particularly high activity with respect to a ketone having adjacent carbonyl groups, such as 2,3-pentanedione, 2,3-hexanedione, or 3,4-hexanedione.

By causing the enzyme of the present invention to act on a prochiral ketone, an optically active alcohol corresponding to the substrate is obtained.

For example, by causing the protein of the present invention to act on some different prochiral ketones, such as 2,3-pentanedione, 2,3-hexanedione, and 3,4-hexanedione, it is possible to obtain (R)-2,3-pentanediol, (R)-2,3-hexanediol, and (R)-3,4-hexanediol, respectively.

The process of causing the protein of the present invention to act on a ketone is not particularly limited. For example, it is possible to cause an expression product to act on a ketone. More specifically, it is possible to cause a transformant for expressing the protein of the present invention, such as a transformant obtained by transforming with a recombinant vector containing the polynucleotide of the present invention, to act on a ketone.

The transformant may be any kind insofar as the protein of the present invention can be effectively expressed. Examples of the transformants include a transformant for expressing the protein of SEQ ID NO: 1 such as *Escherichia coli* transformed by pSE-HOG.

The transformant may co-express an enzyme for recovering NADH, for example, glucose dehydrogenase or formic dehydrogenase, with the enzyme of the present invention.

The transformant may be subjected to appropriate treatment. Examples of the processed transformants include microorganisms treated with an organic solvent, such as surfactant or toluene, to change cell membrane permeability; freeze-dried or spray-dried cell bodies; cell-free extracts, half-purified as required, obtained by pulverizing a cell body with enzyme or glass beads; purified enzymes; immobilized enzymes obtained by immobilizing a transformant or enzyme; and immobilized microorganisms.

It is also possible to cause a cell producing the protein of the present invention to act on a ketone.

The process for reacting the protein of the present invention is performed either in water, an organic solvent or in a mixed solvent of water and an organic solvent. Examples of the organic solvents include acetic acid ethyl, acetic acid butyl, toluene, chloroform, and n-hexane.

The reaction process may also be performed using immobilized enzymes, membrane reactors or the like.

In the reaction step, the reaction temperature is 5 to 50° C., preferably 5 to 35° C.; and the pH is generally 5 to 8, preferably 6 to 7.

The substrate concentration is 0.01 to 90%, preferably 0.1 to 30%. The enzyme concentration is generally 0.01 to 10 unit/ml, preferably 0.1 to 5 unit/ml.

The substrate may be added all at once in the beginning of the reaction; however, it is more preferable to add the substrate in a continuous or discontinuous manner to prevent excessive increase of the substrate concentration in the reaction mixture.

As required, the reaction system may contain coenzyme NADH of about 0.1 to 20 mM, preferably about 1 to 10 mM.

The reaction also derives $NAD^+$ from NADH. The $NAD^+$ may be recovered to NADH using the $NAD^+$ reduction ability of the microorganism (C1 compound metabolic pathway of methylotroph, etc).

For example, it is possible to recover NADH using a microorganism, either processed or unprocessed, containing glucose dehydrogenase, alcoholdehydrogenase, formic dehydrogenase, amino acid dehydrogenase, organic acid dehydrogenase (malate dehydrogenase etc.), etc.; or purified or partially-purified enzymes.

These components for the NADH recovery reaction can be added to the reaction system for producing the optically active alcohol of the present invention.

However, it may be possible to omit this extra NADH recovery reaction system when the optically active alcohol production is performed using a live microorganism transformed by a recombinant vector containing the polynucleotide of the present invention. More specifically, by selecting a host from the microorganisms having high NADH recovery activity, the reductive reaction using a transformant can be more efficiently performed without using an NADH recovery enzyme.

The expressions of the NADH recovery enzyme and the NAD-dependent R-specific alcohol dehydrogenase, and the reducive reaction can be more efficiently performed by introducing NADH recoverble genes such as glucose dehydrogenase, alcoholdehydrogenase, formic dehydrogenase, amino acid dehydrogenase, or organic acid dehydrogenase (malate dehydrogenase etc.) to a host, together with the DNA for encoding the NAD-dependant R-specific alcohol dehydrogenase of the present invention. The introduction of such two or more kinds of genes into the host is performed by a method for introducing two or more genes into a single vector, a method for introducing one or both of the genes in the chromosome, or a method for transforming the host by a recombinant vector obtained by separately introducing plural genes in separate vectors of different replication origins, so as to eliminate the problem of incompatibility.

When introducing two or more kinds of genes into a single vector, it is possible to connect the regions involved in expression control, such as a promoter, terminator etc. to each gene, or express the genes as operons such as lactose operon containing a plurality of cistrons.

Examples of NADH recovery enzymes include glucose dehydrogenases derived from genus *Bacillus*, genus *Pseudomonas*, genus *Thermoplasma* or the like. A preferred enzyme is a recombinant vector incorporating glucose dehydrogenase gene derived from *Bacillus subtilis*. Additionally, formic dehydrogenases derived from genus *Mycobacterium*, such as a recombinant vector incorporating a formic dehydrogenase derived from *Mycobacterium vaccae*, are also useful as the NADH recovery enzyme.

(6-2) Process using Stereoselective Oxidative Reaction of Racemic Alcohol

The present invention provides a process for causing the protein of the present invention to act on racemic alcohol to cause stereoselective oxidative reaction, thereby producing optically active alcohol.

Examples of racemic alcohols include alkane diols having adjacent hydroxyl groups, such as 1,2-propanediol, 1,2-butanediol, 2,3-butanediol, 1,2-pentanediol, 1,2-hexanediol, 1,2-heptanediol or 1,2-octanediol.

Among them, the protein of the present invention has particularly high activity and stereoselectivity with respect to long-chain alkane diol, such as 1,2-octanediol.

Acting on racemic alcohol, the protein of the present invention dehydrogenates R-configuration alcohol more preferentially than the S-configuration alcohol, and produces a corresponding ketone body. By isolating the obtained ketone body, it is possible to selectively obtain S-configuration alcohol. By further reducing the isolated ketone body, it is possible to selectively obtain R-configuration alcohol.

For example, by causing the protein of the present invention or a transformant to act on (R,S)-1,2-octanediol, (R)-1,2-octanediol is selectively oxidized to 1-hydroxy-2-octanone. By isolating the 1-hydroxy-2-octanone, it is possible to obtain highly pure (S)-1,2-octanediol.

The process of causing the protein of the present invention to act on racemic alcohol is not particularly limited. For example, it is possible to cause an expression product to act on alcohol. More specifically, it is possible to cause a transformant for expressing the protein of the present invention, such as a transformant obtained by transforming with a recombinant vector containing the polynucleotide of the present invention, to act on ketone. Examples of such transformants include a transformant for expressing the protein of SEQ ID NO: 1 such as *Escherichia coli* transformed by pSE-HOG.

The transformant may be any kind insofar as the protein of the present invention can be effectively expressed. The transformant may co-express an enzyme for recovering $NAD^+$, such as lactate dehydrogenase, with the enzyme of the present invention.

The transformant may be subjected to appropriate treatment. Examples of the processed transformants include microorganisms treated with an organic solvent, such as surfactant or toluene, to change cell membrane permeability; freeze-dried or spray-dried cell bodies; cell-free extracts, half-purified as required, obtained by pulverizing a cell body with enzyme or glass beads; purified enzymes; immobilized enzymes obtained by immobilizing a transformant or enzyme; and immobilized microorganisms. It is also possible to cause a cell producing the protein of the present invention to act on a ketone.

The process for reacting the protein of the present invention is performed either in water, an organic solvent or in a mixed solvent of water and an organic solvent. Examples of the organic solvents include acetic acid ethyl, acetic acid butyl, toluene, chloroform, and n-hexane.

The reaction process may also be performed using immobilized enzymes, membrane reactors or the like.

In the reaction step, the reaction temperature is 5 to 50° C., preferably 5 to 35° C. The pH is generally 7 to 9, preferably 8 to 9.

The substrate concentration is 0.01 to 90%, preferably 0.1 to 30%. The enzyme concentration is generally 0.01 to 10 unit/ml, preferably 0.1 to 5 unit/ml.

The substrate may be added all at once in the beginning of the reaction; however, it is more preferable to add the substrate in a continuous or discontinuous manner to prevent excessive increase of the substrate concentration in the reaction mixture.

As required, the reaction system may contain coenzyme NAD of about 0.1 to 20 mM, preferably about 1 to 10 mM.

This oxidization reaction also produces NADH, which is converted into $NAD^+$ due to the function of the microorganism to recover $NAD^+$ from NADH.

It is also possible to recover $NAD^+$ by adding an enzyme having an activity to oxidize NADH to $NAD^+$, such as lactate dehydrogenases, glutamate dehydrogenases, glucose dehydrogenases, NADH dehydrogenases, NADH oxidases or the like; or processed or unprocessed microorganisms containing these enzymes.

Further, by creating a transformant that co-expresses an enzyme for recovering $NAD^+$ from NADH with the enzyme of the present invention, it is possible to efficiently perform $NAD^+$ recovery reaction and stereoselective oxidative reaction.

(6-3) Purification of Optically Active Alcohol

The aforementioned method (6-1) or (6-2) may comprise a step of purifying an optically active alcohol.

The purification of an optically active alcohol can be performed using an appropriate combination of two or more of: cell body/protein centrifugation, separation by membrane treatment, solvent extraction, distillation, crystallization and the like.

For example, the purification is performed as follows. A reaction liquid containing a transformant is first centrifuged to remove the microorganism bodies, and the residual cells and protein are removed using an ultra filtration membrane, followed by extraction using acetic acid ethyl, acetic acid butyl, toluene, hexane, benzene, methyl isobutylketone, methyl tertially butyl ether, butanol etc. The extract is distilled as such or is concentrated under reduced pressure to obtain an optically active alcohol.

To obtain a reaction product with superior purity, the obtained alcohol can be further purified by precise distillation, silica gel column chromatography or the like.

The optical purity of the optically-active alcohol of the present invention is preferably not less than 80% e.e., more preferably not less than 90% e.e., particularly preferably not less than 98% e.e.

The "optical purity" represents a value obtained by the following calculation.

$$optical\ purity = (R-S/R+S)\ or\ (S-R/R+S) \times 100(\%)$$

(R, S respectively represent right and left enantiomers in the sample.)

7. Process of Producing Useful Compound from Glycerol

The protein of the present invention, i.e., alkane polyol dehydrogenase, performs well as a dehydrogenase for glycerol.

For example, the glycerol dehydrogenase of the present invention is induced in *Pichia ofunaensis* (formerly known as *Hansenula ofunaensis*) by glycerol. The first reaction of glycerol metabolization of microorganisms is phosphorylation by the glycerol kinase in most of the cases, and it is very rare to use such oxidization using a glycerol dehydrogenase. With this characteristic, this enzyme of the present invention derived from *Pichia ofunaensis* or the like has significantly high glycerol dehydrogenating activity.

Glycerol is cheap and easy to obtain, and therefore is widely used. The *Pichia ofunaensis*-derived glycerol dehydrogenase of the present invention is thus made by growing an inexpensive glycerol substrate, and metabolizing it into a material through oxidization. Accordingly, the glycerol dehydrogenase of the present invention enables economical and efficient production of added-value substances inducible from glycerol.

Further, the glycerol dehydrogenase of the present invention can also be used as a measurement enzyme or a component of a measurement kit to be used for, for example, enzyme measurement using glycerol or a derivative thereof as a substrate.

For example, the glycerol dehydrogenase of the present invention can be used as a triacylglycerol quantifying enzyme as follows. The triacylglycerol in the serum lipid is hydrolyzed, and the generated glycerol is quantified using the glycerol dehydrogenase of the present invention.

Further, the glycerol dehydrogenase of the present invention can also be used as an alkaline phosphatase activity quantifying enzyme as follows. An alkaline phosphatase is caused to act on a substrate of glycerol-3-phosphate, and the released glycerol is quantified using the glycerol dehydrogenase of the present invention.

The present invention provides a process for producing dihydroxyacetone or a derivative thereof, comprising causing the protein of the present invention to act on glycerol.

The process of causing the protein of the present invention to act on glycerol is not particularly limited. For example, it is possible to cause an expression product to act on a glycerol. More specifically, it is possible to cause a transformant for expressing the protein of the present invention, such as a transformant obtained by transforming with a recombinant vector containing the polynucleotide of the present invention, to act on glycerol.

The transformant may be any kind insofar as the protein of the present invention can be effectively expressed. Examples of the transformants include a transformant for expressing the protein of SEQ ID NO: 1 such as *Escherichia coli* transformed by pSE-HOG.

The transformant may co-express an enzyme for recovering NAD$^+$, for example, lactate dehydrogenase, glucose dehydrogenase or formic dehydrogenase, with the protein of the present invention.

The transformant may be subjected to appropriate treatment. Examples of the processed transformants include microorganisms treated with an organic solvent, such as surfactant or toluene, to change cell membrane permeability; freeze-dried or spray-dried cell bodies; cell-free extracts, half-purified as required, obtained by pulverizing a cell body with enzyme or glass beads; purified enzymes; immobilized enzymes obtained by immobilizing a transformant or enzyme; and immobilized microorganisms.

It is also possible to causes a cell producing the protein of the present invention to act on glycerol.

The process for reacting the protein of the present invention is performed either in water, an organic solvent or in a mixed solvent of water and an organic solvent. Examples of the organic solvents include acetic acid ethyl, acetic acid butyl, toluene, chloroform, and n-hexane.

The reaction process may also be performed using immobilized enzymes, membrane reactors or the like.

In the reaction step, the reaction temperature is 5 to 50° C., preferably 5 to 35° C.; and the pH is generally 7 to 9, preferably 8 to 9.

The substrate concentration is 0.01 to 90%, preferably 0.1 to 30%. The enzyme concentration is generally 0.01 to 10 unit/ml, preferably 0.1 to 5 unit/ml.

The glycerol may be added all at once in the beginning of the reaction; however, it is more preferable to add the substrate in a continuous or discontinuous manner to prevent excessive increase of the substrate concentration in the reaction mixture.

As required, the reaction system may contain coenzyme NAD$^+$ of about 0.1 to 20 mM, preferably about 1 to 10 mM.

The protein of the present invention has an excellent oxidization activity with respect to glycerol, and thereby efficiently produces corresponding dihydroxyacetone.

Dihydroxyacetone is a compound commonly used in skin-coloring cosmetics to change the skin color to a healthier tone, which is particularly popular among Caucasians who must avoid excessive exposure to ultraviolet light to reduce the risk of carcinoma cutaneum. The safety of dihydroxyacetone has been approved by the U.S. Food and Drug Administration.

Dihydroxyacetone is an only product resulting from the reaction of glycerol dehydrogenase of the present invention with inexpensive glycerol. Accordingly, the present invention enables mass production of useful dihydroxyacetone at low cost.

The resulting dihydroxyacetone may be further subjected to any known reaction to be converted into a substance.

Examples of the substances to be derived from dihydroxyacetone include dihydroxyacetone phosphate, glyceraldehyde 3-phosphate; and succinic acid, fumaric acid, malic acid, aspartic acid, etc. produced by the tricarboxylic acid cycle.

The protein of the present invention facilitates the oxidization of glycerol, and thereby efficiently produces dihydroxyacetone or a derivative thereof at low coat.

EFFECT OF THE INVENTION

The present invention provides a protein having an excellent alkane polyoldehydrogenation activity, and usage of the protein.

The protein of the present invention has an excellent alkane polyoldehydrogenation activity.

The protein of the present invention has an excellent oxidization activity particularly with respect to long-chain alkane polyol. The protein of the present invention has an excellent dehydrogenation activity, particularly with respect to alcohols having adjacent hydroxyl groups.

The protein of the present invention preferentially oxidizes an R-configuration hydroxyl group, and has a high substrate specificity. The protein of the present invention has an excellent oxidization activity particularly with respect to glycerol.

The protein of the present invention has an excellent reduction activity with respect to ketone, particularly to long-chain alkanones. The activity is more intensively exhibited particularly with respect to a ketone having adjacent carbonyl groups.

Using such a superior protein, the present invention enables efficient production of an optically active alcohol useful as a starting material of a chiral compound etc., at low cost.

The present invention also enables efficient production of a ketone body, particularly a prochiral ketone body useful for the production of chiral compounds, using the protein.

The protein of the present invention allows for efficient production of added-value substances from inexpensive glycerol.

The present invention also provides a polynucleotide for coding the protein, as well as a transformant for expressing the protein. Using the polynucleotide and the transformant of the present invention, it is possible to perform mass production of the aforementioned protein with the superior characteristic.

As explained, the present invention provides an enzyme useful for efficient production of added-value substances, and usage of the enzyme.

BEST MODE FOR CARRYING OUT THE INVENTION

Figure 1:
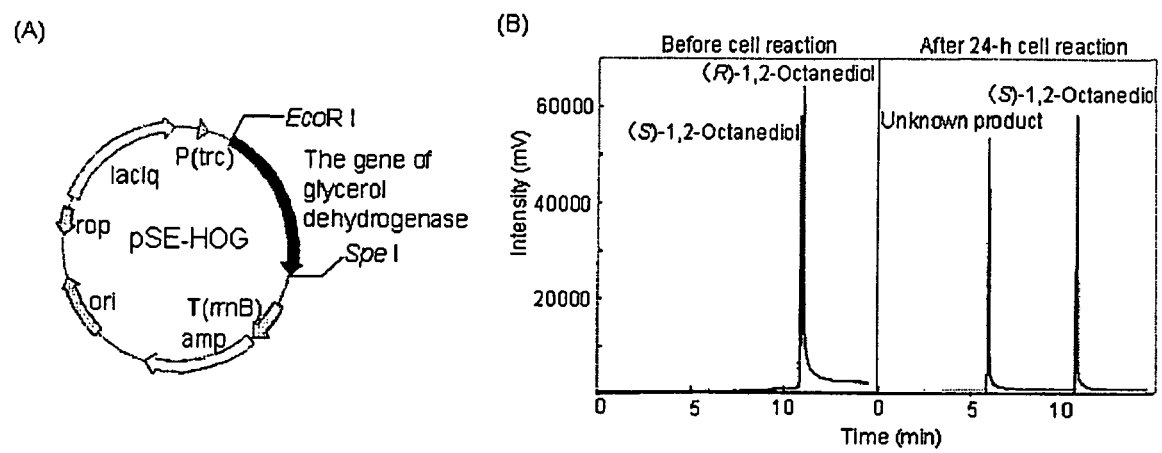
FIG. 1(A) is a diagram showing the construction of the expression plasmid (pSE-HOG), into which an alkane polyol dehydrogenase gene derived from *Pichia ofunaensis* is inserted. In the map of the plasmid, "P(trc)" represents a trc promoter; "T(rrnB)" represents an rrnBT1T2 terminator; "amp" represents a β-lactase gene exhibiting ampicillin resistance; "ori" represents the replication origin of the plasmid; "rop" represents a ROP-protein gene; and "laqIq" represents a lactose repressor. "The gene of glycerol dehydrogenase" refers to the gene of the alkane polyol dehydrogenase of the present invention.
FIG. 1(B) is a graph showing the detection results obtained by causing *Escherichia coli* HB101 strain containing pSE-HOG to act on racemic 1,2-octanediol, and observing R- and S-configurations of 1,2-octanediol with a gas chromatograph equipped with a FID detector. The left half of FIG. 1(B) shows the detection results before the reaction, and the right half is the detection result after the reaction was continued for 24 hours. The abscissa shows the retention time.

Hereinafter, the present invention will be described in more detail with reference to the following Examples and Comparative Examples. The present invention is not, however, limited thereto.

EXAMPLE 1

Production of Alkane Polyol Dehydrogenase

1-1: Culture of *Pichia ofunaensis*

*Pichia ofunaensis* AKU4328 (obtained from Kyoto University) was inoculated into 10 tubes containing 5 mL of basal medium A containing 1% glucose, and cultivated to mid-log phase at 30° C. The obtained cells were then inoculated into 10 tubes containing 500 mL of basal medium A containing 1% glycerol, and cultivated to mid-log phase at 30° C. The thus-obtained culture solutions were subjected to centrifugal separation. Thereby, cells for use in purifying enzymes were obtained.

1-2: Purification of Alkane Polyol Dehydrogenase

The entire purification process was performed at 4° C., unless otherwise indicated. The cells (20 g wet cell weight) prepared as above in 1-1, were suspended in buffer solution A (100 mM potassium phosphate buffer solution (pH 7.0) and 1 mM dithiothreitol (hereinafter simply referred to as DTT)). The resulting suspension was mixed with 100 ml of glass beads, and disrupted with a bead beater (produced by Bio-Spec, Bartlesville, USA).

The resulting disrupted cell liquid was subjected to centrifugal separation under an acceleration of 9,000 g for 30 minutes. Thereby, the supernatant thereof as a cell extract was obtained.

The obtained cell extract was allowed to adsorb to a DEAE-cellulose column (diameter 4.0 cm×height 3.5 cm, produced by Wako Pure Chemical Ind. Ltd., Osaka) that was pre-equilibrated with buffer solution A. Thereafter, the gradient of 0-1 M potassium chloride was applied to buffer solution A to elute protein at a flow rate of 1 ml/min.

The eluted active fractions were collected, and dialyzed against buffer solution A containing 40% saturated ammonium sulfate. The resulting dialyzed product was then allowed to absorb to a butyl-Toyopearl 650S column (1.5×10 cm, produced by Tosoh Corporation, Tokyo) that was pre-equilibrated with the same buffer solution. The resulting column was washed with the same buffer solution, and protein was eluted with a gradient of 40-0% saturated ammonium sulfate.

The eluted active fractions were collected, and dialyzed against buffer solution A containing 0.1 M potassium chloride.

The resulting dialyzed product was loaded onto a Superdex 200 HR16/60 column (produced by Amersham Biosciences, Tokyo, Japan) that was pre-equilibrated with buffer solution A containing 0.1 M potassium chloride. Then, the elution was conducted at a flow rate of 0.5 ml/min using buffer solution A containing 0.1 M potassium chloride.

Table 1 shows the summary of the purification process. Table 1 also shows the enzyme activities of the obtained protein.

TABLE 1

|  | Protein (mg) | Total Activity (U) | Specific Activity (U/mg) | Purification (fold) | Yield (%) |
|---|---|---|---|---|---|
| Cell Extract | 201 | 110 | 0.55 | 1 | 100 |
| DEAE-Cellulose | 4.91 | 35.4 | 7.2 | 13 | 32 |
| Butyl-Toyopearl | 0.51 | 21.5 | 42 | 76 | 20 |
| Superdex 200 | 0.09 | 4.6 | 51 | 93 | 4.2 |

In connection with the enzyme activity, a reaction mixture containing 100 mM glycerol, 2 mM NAD$^+$ and enzyme was allowed to react in a 100 mM potassium phosphate buffer solution (pH 8.0) at 25° C.; subsequently, the change, due to NADH formation, of absorbance (molar absorption coefficient 6,220 M$^{-1}$·cm$^{-1}$) at 340 nm was measured and analyzed. 1 U was defined as the amount of enzyme that catalyzes the formation of 1 μmol of NADH per minute.

1-3: Determination of Molecular Weight

The subunit molecular weight of the purified protein (hereinafter also referred to as "alkane polyol dehydrogenase") was calculated using 12.5% sodium dodecyl sulfate-polyacrylamide gel electrophoresis (SDS-PAGE) to be about 39,000.

The molecular weight of the purified alkane polyol dehydrogenase was calculated from the elution time of the aforementioned gel filtration chromatography with the Superdex 200HR16/60 column, with reference to the elution times of standard proteins produced by GE Healthcare Bio-Science KR, phosphorylase b (molecular weight: 97,000), cow serum albumin (molecular weight: 66,000), ovalbumin (molecular weight: 45,000), carbonic anhydrase (molecular weight: 30,000), and trypsin inhibitor (molecular weight: 21,000). The calculated molecular weight of the purified alkane polyol dehydrogenase was about 58,000.

The above molecular weight was calculated assuming that the purified enzyme was spherical; therefore, the molecular weight was theoretically deemed to be an integral multiple of a subunit molecular weight. The results, however, reveal that the ratio thereof was about 1.5, which implies that the obtained purified protein was not spherical in a solution, having a configuration that is different from those of many other proteins.

EXAMPLE 2

Analysis of Amino Acid Sequence and Base Sequence

2-1: Analysis of N-Terminal and Internal Amino Acid Sequence

The amino acid sequence was determined with respect to the N-terminal of the purified enzyme obtained in Example 1 and peptide fragments obtained by digestion with protease V8 by means of a protein sequencer (ABI Prism 310 genetic analyzer, produced by Applied Biosystems) and a reaction mixture kit (Dye Terminator Cycle Sequencing Kit).

The N-terminal amino acid sequence of the purified enzyme was thereby determined as:

MKGLLYYKTGDIRYSEDVEE.        (SEQ ID NO: 3)

Further, the purified enzyme obtained in Example 1 was subjected to SDS-PAGE and then partially digested, in a stacking gel, with protease V8 in an amount of ¹/₂₀ at room temperature for 1 hour. The peptide fragments (the partially digested products) were isolated by electrophoresis and then blotted onto a PVDF (polyvinylidene difluoride) membrane. Thereby, the amino acid sequences thereof were analyzed and determined as below.

```
ILSSHDVKIR,        (SEQ ID NO: 4)

ATTHLSDA,          (SEQ ID NO: 5)
and

LKALLPENGGFDA.     (SEQ ID NO: 6)
```

As above, three internal amino acid sequences of the purified enzyme were determined.

2-2: Purification of Chromosomal DNA from Pichia ofunaensis

Pichia ofunaensis AKU4328 was cultivated in basal medium A containing 1% methanol. The purification of chromosomal DNA was carried out in accordance with the method disclosed in Meth. Cell Biol., 29, 39-44 (1975).

2-3: Cloning of Core Region of Gene Encoding Alkane Polyol Dehydrogenase

Based on the amino acid sequences obtained above in 2-1, primers 1 and 2 were synthesized as below.

```
Primer 1:
5'-TAYTAYAARACNGGNGAYAT-3',   (SEQ ID NO: 7)
and

Primer 2:
5'-GCRTCRAANCCNCCRTTYTC-3'.   (SEQ ID NO: 8)
```

The primer 1 corresponds to Y at position 6 to I at position 12 in the N-terminal sequence, MKGLLYYKTGDIRYSEDVEE.

The primer 2 corresponds to E at position 7 to A at position 13 in the internal amino acid sequence, LKALLPENGGFDA.

PCR was performed in the presence of the primers above under the following conditions using, as template, the chromosomal DNA obtained above in 2-2. Utilizing 50 µL of reaction mixture containing 50 ng of the chromosomal DNA, 25 pmol each of the primers, 20 nmol each of dNTPs, 1.25 U of EX Taq DNA polymerase (produced by Takara Bio, Inc.,) and Ex Taq buffer solution, a heat treatment was carried out at 94° C. for 10 minutes, followed by 30 cycles at 94° C. for 1 minute; at 56° C. for 1 minute; and at 72° C. for 1 minute, and followed finally by 1 cycle at 72° C. for 10 minutes.

The resulting PCR product was purified by isolation by means of agarose electrophoresis, which was inserted into pCR2.1-TOPO (produced by Invitrogen Corporation) so that the base sequence of the inserted DNA fragment was analyzed. The obtained core region comprises a sequence of 766 bp.

2-4: Cloning of 5'-Flanking Region of Core Region of the Gene Encoding Alkane Polyol Dehydrogenase The cloning of 5'-flanking region of core region of the gene was performed using a Takara LA PCR in vitro Cloning Kit (produced by Takara Bio, Inc.,). PCR was performed under the following conditions.

Utilizing 50 µL of reaction mixture containing 0.5 µg of ligated DNA, 25 pmol each of the primers, 20 nmol each of dNTPs, 5 U of LA Taq DNA polymerase (produced by Takara Bio, Inc.,) and LA Taq buffer solution, PCR was performed for 30 cycles at 94° C. for 30 seconds; at 55° C. for 30 seconds; and at 72° C. for 4 minutes.

The following primer S1 was used as a primer:

```
Primer S1
5'-ATCACCAGGTTTCACCCTAGTGAC-3'.   (SEQ ID NO: 9)
```

2-5: Cloning of 3'-Flanking Region of Core Region of the Gene Encoding Alkane Polyol Dehydrogenase Cloning of the 3'-flanking region of the core region was performed in the same manner as for the 5'-flanking region, using a Takara LA PCR in vitro Cloning Kit (produced by Takara Bio, Inc.).

PCR was performed under the following conditions.

Utilizing 50 µL of reaction mixture containing 0.5 µg of ligated DNA, 25 pmol each of the primers, 20 nmol each of dNTPs, 5 U of LA Taq DNA polymerase (produced by Takara Bio, Inc.,) and LA Taq buffer solution, PCR was performed for 30 cycles at 94° C. for 30 seconds; at 55° C. for 30 seconds; and at 72° C. for 4 minutes.

The following primer S2 was used as a primer:

```
Primer S2
5'-GGAATGCGCGAAGTTTAAACCAGG-3'.   (SEQ ID NO: 10)
```

2-6: Entire Open Reading Frame (ORF) Analysis of the Gene Encoding Alkane Polyol Dehydrogenase The base sequences obtained above in 2-4 and 2-5, and the base sequence of the core region obtained in 2-3 were assembled. Thereby, the entire open reading frame (ORF) of the alkane polyol dehydrogenase was revealed.

The base sequence of the obtained ORF is shown in SEQ ID NO: 2 in the Sequence Listing.

ORF encoded a polypeptide containing 1,131 bases and 376 amino acids and having a molecular weight of 40,232.

EXAMPLE 3

Transformant Containing Alkane Polyol Dehydrogenase Gene

3-1: Construction of Expression Plasmid pSE-HOG

HOG-ATG1 and HOG-TAG1 were synthesized as a PCR primer, and PCR was performed under the following conditions. The sequence of HOG-ATG1 is shown below.

```
                                  (SEQ ID NO: 11)
5'-GGAATTCTATAATGAAAGGATTGCTCTATT-3'
```

The sequence of HOG-TAG1 is shown below.

```
                                  (SEQ ID NO: 12)
5'-GGACTAGTCTACACTTCATCAGGAGTAACA-3'
```

Utilizing 50 µL of reaction mixture containing 50 ng of the chromosomal DNA, 25 pmol each of the primers, 20 nmol each of dNTPs, 1.25 U of EX Taq (produced by Takara Bio, Inc.,) and EX Taq buffer solution, PCR was performed for 30 cycles at 94° C. for 10 minutes; at 94° C. for 1 minute; at 58° C. for 1 minute and at 72° C. for 1 minute.

The obtained amplified DNA fragments were treated with EcoRI and Spe I, and then inserted between the trc promoter and rrnB terminator of pSE420D that was treated beforehand with EcoRI and Spe I. Thereby, an expression vector, pSE-HOG, was constructed (see FIG. 1(A)).

The obtained pSE-HOG was introduced into *Escherichia coli* HB101 in accordance with the instruction manual supplied with an Electro Cell 600 produced by Genetronics.

3-2: Production of Alkane Polyol Dehydrogenase using *Escherichia Coli* HB101 Strain The *Escherichia coli* HB101 strain containing the pSE-HOG was cultivated in LB medium containing ampicillin. When the absorbance at 600 nm was 0.5, 0.1 mM IPTG was added thereto. Six hours after the addition, cells were harvested by centrifugal separation.

The obtained cells were suspended in a cell disruption solution (100 mM potassium phosphate buffer solution (pH 8.0)). The cell bodies therein were disrupted using a mini bead beater (produced by BioSpec Products), then subjected to centrifugal separation for 10 minutes under an acceleration of 16,000 g. Thereby, the supernatant thereof as a cell extract was obtained.

The amount of the alkane polyol dehydrogenase expressed from the *Escherichia coli* HB101 strain was about 8.2% of the soluble proteins.

EXAMPLE 4

Properties of Alkane Polyol Dehydrogenase

4-1: Activity Measurement

The alkane polyol dehydrogenase obtained in Example 1 was utilized to measure the enzyme activities in the following manner.

Oxidative Activity

Each reaction mixture containing each of the substrates at each concentration as shown in Table 2, 2 mM $NAD^+$, and enzyme was respectively reacted in 100 mM potassium phosphate buffer solutions (pH 8.0) at 25° C.; subsequently, the change, due to NADH formation, of absorbance (molecular absorption coefficient 6,220 $M^{-1} \cdot cm^{-1}$) at 340 nm was observed. 1 U was defined as the amount of enzyme that catalyzes the formation of 1 μmol of NADH per minute.

Reduction Activity

Each reaction mixture containing each of the substrates at each concentration as shown in Table 3, 0.2 mM NADH, and enzyme was respectively reacted in 100 mM potassium phosphate buffer solutions (pH 6.0) at 25° C.; subsequently, the change, due to NADH reduction, of absorbance (molecular absorption coefficient 6,220 $M^{-1} \cdot cm^{-1}$) at 340 nm was observed. 1 U was defined as the amount of enzyme that catalyzes the reduction of 1 μmol of NADH per minute.

Table 2 shows the measurement results regarding the oxidative activity. Table 3 shows the measurement regarding the reduction activity.

TABLE 2

Measurement of Oxidative Activity

| Substrate | Concentration (mM) | Activity (U/mg) |
|---|---|---|
| Glycerol | 100 | 39.1 |
| Methanol | 100 | ND |
| Ethanol | 100 | ND |
| 1-Propanol | 100 | ND |
| Isopropanol | 100 | 1.45 |
| 1-Butanol | 100 | ND |
| 2-Butanol | 100 | <0.1 |
| 1-Pentanol | 100 | ND |
| n-Hexanol | 10 | ND |
| 2-Heptanol | 10 | ND |
| 2-Octanol | 10 | ND |
| Benzyl alcohol | 10 | ND |
| 3-Hydroxy-2-butanone | 100 | 0.55 |
| 1,2-Propanediol | 100 | 71.7 |
| 1,3-Propanediol | 100 | ND |
| 3-Amino-1,2-propanediol | 100 | ND |
| 2-Phenyl-1,2-propanediol | 10 | ND |
| 1,2-Butanediol | 100 | 61.0 |
| 1,3-Butanediol | 100 | 6.0 |
| 2,3-Butanediol | 100 | 50.0 |
| 1,2-Pentanediol | 100 | 99.3 |
| 2,4-Pentanediol | 100 | 2.53 |
| 1,2-Hexanediol | 100 | 38.4 |
| 2,5-Hexanediol | 100 | 0.77 |
| 1,2-Heptanediol | 10 | 27.8 |
| 1,2-Octanediol | 5 | 64.3 |

TABLE 3

Measurement of Reduction Activity

| Substrate | Concentration (mM) | Activity (U/mg) |
|---|---|---|
| Dihydroxyacetone | 100 | 92.7 |
| Formaldehyde | 100 | 0.57 |
| 2-Butanone | 100 | 0.40 |
| 2-Pentanone | 100 | 3.71 |
| 2-Hexanone | 10 | ND |
| 3-Hexanone | 10 | 1.39 |
| Cyclohexanone | 10 | 0.28 |
| 1-Hydroxy-2-butanone | 100 | 5.84 |
| 3-Hydroxy-2-butanone | 100 | 102 |
| Acetol | 100 | 64.9 |
| 2,3-Pentanedione | 5 | 73.8 |
| 2,3-Hexanedione | 5 | 67.5 |
| 3,4-Hexanedione | 5 | 32.8 |

4-2: Measurement Result of Activities

Oxidative Activity

As shown in Table 2, the purified enzyme did not have oxidative activity toward primary alcohols, such as methanol, ethanol, 1-propanol, 1-butanol, 1-pentanol, n-hexanol, benzyl alcohol and the like.

The purified enzyme showed a weak oxidative activity toward isopropanol and 2-butanol, but no activity was observed toward secondary alcohols having a single hydroxyl group, such as 2-heptanol, 2-octanol, and the like.

In contrast, diols, such as 1,2-propanediol, 1,2-butanediol, 2,3-butanediol, 1,2-pentanediol, 1,2-hexanediol, 1,2-heptanediol, 1,2-octanediol, and the like, were well-oxidized. However, only a weak oxidative activity was observed with respect to diols, such as 1,3-butanediol, 2,4-pentanediol, 2,5-hexanediol, and the like.

The above results reveal that the purified enzyme has a higher oxidative activity particularly toward alcohols having two adjacent hydroxyl groups.

Reduction Activity

As shown in Table 3, the purified enzyme has a high reduction activity against dihydroxyacetone, 3-hydroxy-2-butanone, acetol, 2,3-pentanedione, 2,3-hexanedione, 3,4-hexanedione, and the like.

4-3: Substrate Specificity of Alkane Polyol Dehydrogenase

The substrate specificity of the protein of the present invention was analyzed using the purified enzyme obtained in Example 1 and the transformant (*E. coli* HB101 (pSE-HOG)) obtained in Example 3. For comparison, the same analysis was conducted with respect to a transformant (*E. coli* HB101 (pSE420D)) that was produced in the same manner as for *E. coli* HB101 (pSE-HOG), except that the plasmid (pSE420D) in which the relevant enzyme gene was not inserted was used.

Measurement was performed in the same manner as in the activity measurements described earlier in 4-1.

Table 4 shows the results.

TABLE 4

| Substrate | Concentration (mM) | Purified Enzyme (U/mg) | E. coli HB101 (pSE-HOG) (U/mg) | E. coli HB101 (pSE-420D) (U/mg) |
|---|---|---|---|---|
| (R,S)-1,2-Octanediol | 5 | 64.3 | 0.53 | ND |
| (S)-1,2-Octanediol | 5 | ND | ND | ND |
| (R)-1,2-Propanediol | 100 | 89.2 | 0.80 | <0.1 |
| (S)-1,2-Propanediol | 100 | 36.4 | 0.29 | <0.1 |
| (2R,3R)-2,3-Butanediol | 100 | 82.1 | 0.72 | ND |
| (2S,3S)-2,3-Butanediol | 100 | 19.4 | 0.12 | ND |
| meso-2,3-Butanediol | 100 | 160 | 1.17 | <0.1 |
| (R)-1,2,4-Butanetriol | 100 | 3.9 | 0.15 | ND |
| (S)-1,2,4-Butanetriol | 100 | ND | ND | ND |

As is shown in Table 4, the purified enzyme and *E. coli* HB101 (pSE-HOG) show an excellent dehydrogenation activity on (R,S)-1,2-octanediol, In contrast, *E. coli* HB101 (pSE420D) does not show the dehydrogenation activity thereon.

The cell extracts of the purified enzyme and *E. coli* HB101 (pSE-HOG) show an oxidative activity on (R,S)-1,2-octanediol, but not on (S)-1,2-octanediol. In light of this, the purified enzyme and *E. coli* HB101 (pSE-HOG) only oxidize (R)-1,2-octanediol. In other words, the purified enzyme and *E. coli* HB101 (pSE-HOG) preferentially oxidize hydroxyl groups in the R-configuration.

The purified enzyme and *E. coli* HB101 (pSE-HOG) also show a high dehydrogenation activity toward 1,2-propanediol and 2,3-butanediol. A significant dehydrogenation activity thereof was observed not only toward 1,2-propanediol and 2,3-butanediol that have hydroxyl group in the R-configuration, but also toward those having hydroxyl group in the S-configuration. In light of this, the higher the carbon numbers thereof, the higher the specificity with respect to the R-configuration of alkane polyol.

The purified enzyme and *E. coli* HB101 (pSE-HOG) have a significant dehydrogenation activity with respect to (R)-1,2,4-butanetriol, but no activity was seen with respect to (S)-1,2,4-butanetriol. In view of this, the purified enzyme and *E. coli* HB101 (pSE-HOG) also have the dehydrogenation activity with respect to polyols having three or more hydroxyl groups. Further, the purified enzyme and *E. coli* HB101 (pSE-HOG) preferentially oxidize hydroxyl groups in the R-configuration.

4-4: Other Properties of Alkane Polyol Dehydrogenase

The following properties were further examined with regard to the purified enzyme obtained in Example 1.

(1) Specific Activity

The purified enzyme had, per 1 mg of the purified protein, about 60 U or more of (R)-1,2-octanediol dehydrogenase activity.

Such activity was measured by causing a reaction mixture containing 5 mM (R)-1,2-octanediol, 2 mM NAD$^+$ and enzyme to react in a 100 mM potassium phosphate buffer solution (pH 8.0) at 25° C., then observing the change, due to NADH formation, of absorbance (molecular absorption coefficient 6,220 M$^{-1}$·cm$^{-1}$) at 340 nm. 1 U was defined as the amount of enzyme that catalyzes the formation of 1 μmol of NADH per minute.

(2) Optimum pH

The optimum pH for glycerol oxidation reaction was about 9, and that for the dihydroxyacetone reduction reaction was about 6.

The optimum pH herein for glycerol oxidation reaction was calculated by causing a reaction mixture containing 500 mM glycerol, 1 mM NAD$^+$, and the purified enzyme to react in a 100 mM buffer solution at various pHs at 25° C., then observing the change, due to NADH formation, of absorbance (molecular absorption coefficient 6,220 M$^{-1}$·cm$^{-1}$) at 340 nm. 1 U was defined as the amount of enzyme that catalyzes the formation of 1 μmol of NADH per minute.

As a buffer solution, NH$_4$Cl—NH$_4$OH (pH 8 to 11), K$_2$HPO$_4$—KH$_2$PO$_4$ (pH 6 to 8), Tris-HCl (pH 7.2 to 9.0) or Tris-maleate (pH 4.7 to 9.4) was utilized.

The optimum pH for a dihydroxyacetone reduction reaction was calculated by causing a reaction mixture containing 1.3 mM dihydroxyacetone, 0.1 mM NADH and the purified enzyme to react in a 100 mM buffer solution at various pHs at 25° C., then observing the change, due to NADH reduction, of absorbance (molecular absorption coefficient 6,220 M$^{-1}$·cm$^{-}$$_1$) at 340 rum. 1 U was defined as the amount of enzyme that catalyzes the reduction of 1 μmol of NADH per minute. Examples of the usable buffer solutions include NH$_4$Cl—NH$_4$OH (pH 8 to 11), K$_2$HPO$_4$—KH$_2$PO$_4$ (pH 6 to 8), Tris-HCl (pH 7.2 to 9.0), or Tris-maleate (pH 4.7 to 9.4).

(3) Optimum Temperature

The optimum temperature for a dihydroxyacetone reduction reaction was about 40° C.

The optimum temperature for a dihydroxyacetone reduction reaction was calculated by causing a reaction mixture containing 100 mM potassium phosphate buffer (pH 6.0), 1.3 mM dihydroxyacetone, 0.1 mM NADH and the purified enzyme to react at 5° C. to 65° C., and observing the change of absorbance (molecular absorption coefficient 6,220 M$^{-1}$·cm$^{-1}$) at 340 nm due to the formation or extinction of NADH. 1 U was defined as the amount of enzyme that catalyzes the reduction of 1 μmol of NADH per minute.

EXAMPLE 5

Production of Optically Active Alcohol

*Escherichia coli* HB101 strain containing the pSE-HOG was obtained in the same manner as in Example 3.

Six hundred mg of the cell (dry cell weight) and racemic 1,2-octanediol (R:S=52:48) were added to 60 ml of KPB buffer (pH 7.0) at a final concentration of 100 mM so that the final concentration of the resulting mixture was 50 mM. The resulting mixture was then shaken, in a 500 ml conical flask, at 150 rpm for 24 hours to be reacted at 30° C.

The resulting reaction mixture was centrifuged under an acceleration of 9,000 g for 30 minutes at 4° C. Thereafter, the supernatant thereof was recovered, and the reaction product was measured as given below.

In the measurement of 1,2-octanediol, the quantification was performed using a gas chromatograph (GC2010, produced by Shimadzu Corporation) equipped with a FID detector. Helium was utilized as a carrier gas (linear velocity: 45.5 cm/sec), and nitrogen was utilized as makeup gas for FID (at a flow rate of 30 ml/min). The obtained supernatant (0.5 μl) was injected onto the Chirasil-DEX CB column (produced by Chrompack, Middelburg, The Netherlands).

The column temperature was kept warm at 110° C. for 1 minute, and then set to increase at 4° C. per minute to 160° C. The temperatures of the inlet and the detector were respectively adjusted to 250° C. and 275° C. The GC/MS analysis was performed using the HP 5890 Series II gas chromatograph (produced by Hewlett Packard, Polo, USA) equipped with an MStation JMS mass-selective detector (produced by JEOL, Tokyo). The detector was operated at 70 eV ionization energy.

FIG. 1(B) shows the measurement results.

The left half of FIG. 1(B) shows the detection result before the reaction, and the right half thereof shows the detection result after the reaction was carried out for 24 hours.

In FIG. 1(B), the abscissa designates the retention time.

As is shown in the right half of FIG. 1(B), with respect to the reaction product after the cell reaction using *E. coli* HB101 (pSE-HOG), (R)-1,2-octanediol was not observed; however, another reaction product was observed.

As for the retention time of the substrates, (S)-1,2-octanediol was 10.6 minutes, (R)-1,2-octanediol was 10.8 minutes, and the reaction product was 5.9 minutes.

When the reaction product (Unknown Product) detected after the cell reaction was examined using an EI mass spectrum, the major ions (m/z) were 144 (1.15%, M$^+$), 113 (100%), and 85 (38.2%). Accordingly, the reaction product was confirmed to be 1-hydroxy-2-octanone.

In view of the above, the cell reaction with *E. coli* HB101 (pSE-HOG) was confirmed to cause an enantioselective oxidation of hydroxyl group, thereby oxidizing (R)-1,2-octanediol to 1-hydroxy-2-octanone.

Consequently, the oxidized (R)-1,2-octanediol was removed after the reaction was continued for 24 hours, and (S)-1,2-octanediol (24 mM>99.9% e.e.) was obtained.

EXAMPLE 6

Production of Ketone

*Pichia ofunaensis* AKU4328 was pre-cultured in medium containing 4 g/L of ammonium chloride, 1 g/L of phosphoric acid 2 hydrogen 1 potassium, 1 g/L of phosphoric acid 1 hydrogen 2 potassium, 0.5 g/L of magnesium sulfate 7 hydrate, 1 g/L of yeast extract, and 1% glucose. Ten hours after the initiation of the main culture in induction medium consisting of a basal medium with 1% glycerol, the cells were harvested. Since the specific activity of glycerol was 3.6 U/mg (protein), it was confirmed that the same protein as the purified enzyme obtained in Example 1 was expressed by 7%.

Two mg/ml each of the thus-obtained cells and a 100 mM potassium phosphate buffer (pH 8.0) containing 10% each of 2,3-butanediol, 1,2-butanediol, and 1,2-propanediol were introduced into a Sakaguchi flask, which was reciprocally shaken at 150 rpm for 20 hours at 30° C. Subsequently, centrifugal separation was carried out to obtain the supernatant thereof. Then, HPLC analysis was performed on the thus-obtained supernatant.

As a result, ketones, which were acetoin, 1-hydroxy-2-butanone and acetol, each corresponding to each of the alcohols were respectively produced by 2.0%, 1.5%, and 2%.

With respect to the reaction of acetol obtained from 1,2-propanediol, when the reaction was carried out for two weeks under the same conditions, while the pH thereof was constantly adjusted to 8, acetol was produced with a theoretical yield of 5%.

In relation to the measurement of the enzyme activity, a reaction mixture containing a 100 mm ammonium chloride/ammonia buffer (pH 9.0), 100 mM glycerol, 2.0 mM NAD$^+$ and an enzyme solution was subjected to a reaction at 25° C.; subsequently, the change, due to NADH formation, of absorbance (molecular absorption coefficient 6,220 M$^{-1}$·cm$^{-1}$) at 340 nm was measured. 1 U refers to the amount of enzyme that catalyzes the formation of 1 μmol of NADH per minute.

L-7100 (Hitachi, Ltd.) was used for the HPLC analysis, Shodex KS-801 (Shimadzu Corp.) was used for the column, and a refractive-index detector L-3350 (Hitachi, Ltd.) was used for the detector.

After the reaction mixture was injected onto a column, the elution was performed at 0.8 ml/min using purified water at 60° C. The retention times were 12.54 minutes for the 2,3-butanediol; 15.07 minutes for the 1,2-butanediol; 12.86 minutes for the 1,2-propanediol; 15.01 minutes for the acetoin; 19.06 minutes for the 1-hydroxy-2-butanone; and 16.18 minutes for the acetol.

EXAMPLE 7

Production of Dihydroxyacetone using Glycerol Dehydrogenase

7-1: Production of Dihydroxyacetone using Purified Enzyme

One pmol of NAD$^+$, 50 μmol of glycerol, 2 units of the purified enzyme obtained in Example 1, 50 μmol of sodium pyruvate and 4 units of porcine heart lactate dehydrogenase (Toyobo Co., Ltd.) were added to 5 ml of a 100 mM Potassium Phosphate Buffer (pH 8.0). The resulting mixture was, in a 30 ml Erlenmeyer flask, rotary shaken at 150 rpm for 12 hours at 35° C.

Consequently, 25 μmol of dihydroxyacetone was obtained.

The dihydroxyacetone and glycerol were quantified using a HPLC (LC-6A: Shimadzu Corp.). Shimpak KS-801 (Shimadzu Corp.) was used for the column, and a Toyo Soda RI-8 refractive-index detector was used for the detector. The reaction mixture was injected onto a column, after which the elution was performed at 0.8 ml/min using purified water. The dihydroxyacetone was eluted at 15.33 minutes, and the glycerol was eluted at 12.04 minutes.

(7-2) Production of Dihydroxyacetone using Cell that Produces Enzyme

*Pichia ofunaensis* AKU4328 was pre-cultured in medium containing 4 g/L of ammonium chloride, 1 g/L of phosphoric acid 2 hydrogen 1 potassium, 1 g/L phosphoric acid 1 hydrogen 2 potassium, 0.5 g/L of magnesium sulfate 7 hydrate, 1 g/L yeast extract, and 1% glucose. Ten hours after the initiation of the main culture in induction medium that consists of a basal medium with 1% glycerol, the cells were harvested. The specific activity of the cells against glycerol was 3.6 U/mg (protein). The cells achieved, per 1 kg of wet cell weight, glycerol dehydrogenation activity of 1,300,000 U.

Two mg/ml of the thus-obtained cells and a 100 nM potassium phosphate buffer (pH 8.0) containing 10% of glycerol were introduced into a Sakaguchi flask. The mixture was reciprocally shaken at 150 rpm for 1 hour at 30° C., and subjected to centrifugal separation. Subsequently, HPLC analysis was performed on the supernatant isolated therefrom.

Consequently, 2% of dihydroxyacetone was obtained.

The activity at this time was measured by causing a reaction mixture containing a 100 mM ammonium chloride/ammonia buffer (pH 9.0), 100 mM glycerol, 2.0 mM $NAD^+$ and an enzyme solution to react at 25° C., then observing the change, due to NADH formation, of absorbance (molecular absorption coefficient 6,220 $M^{-1} \cdot cm^{-1}$) at 340 nm. 1 U refers to the amount of enzyme that catalyzes the formation of 1 μmol of NADH per minute.

L-7100 (Hitachi, Ltd.) was used for the HPLC analysis, Shodex KS-801 (Shimadzu Corp.) was used for the column, and a refractive-index detector L-3350 (Hitachi, Ltd.) was used for the detector.

The invention claimed is:

1. An isolated protein consisting of the amino acid sequence of SEQ ID NO: 1.

2. An isolated polynucleotide selected from:
   (a) a polynucleotide having a nucleic acid sequence that encodes a protein consisting of the amino acid sequence of SEQ ID NO: 1; or
   (b) a polynucleotide having a nucleic acid sequence of SEQ ID NO: 2.

3. A transformant containing a recombinant vector comprising the polynucleotide according to claim 2.

4. A process for producing a protein consisting of the amino acid sequence of SEQ ID NO: 1, comprising the steps of:
   culturing a transformant containing an expression vector comprising a polynucleotide selected from:
   (a) a polynucleotide having a nucleic acid sequence that encodes a protein consisting of the amino acid sequence of SEQ ID NO: 1; or (b) a polynucleotide having a nucleic acid sequence of SEQ ID NO: 2; and
   collecting the expressed protein product of SEQ ID NO: 1.

5. A process for producing a ketone, comprising the step of:
   contacting the protein of claim 1 with alcohol having a hydroxyl group in the R configuration, which is selected from the group consisting of 1,2-pentanediol, 1,2-hexanediol, 1,2-heptanediol and 1,2-octanediol in the presence of NAD to produce the ketone.

6. A process for producing 1-hydroxy-2-octanone, comprising the step of:
   contacting the protein of claim 1 with (R)-1,2-octanediol in the presence of NAD to produce 1-hydroxy-2-octanone.

7. A process for producing an optically-active alcohol, comprising the steps of:

contacting the protein of claim 1 with a racemic mixture of 1,2-pentanediol, 1,2-hexanediol, 1,2-heptanediol, or 1,2-octanediol in the presence of NAD to produce a ketone; and isolating the unreacted optically-active alcohol in the S-configuration.

8. A process for producing an optically-active alcohol, comprising the steps of:

contacting the protein of claim 1 with a racemic mixture of 1,2-octanediol in the presence of NAD to produce 1-hydroxy-2-octanone; and isolating the unreacted optically-active alcohol in the S-configuration.

9. A process for producing dihydroxyacetone, comprising the step of:

contacting the protein of claim 1 with glycerol in the presence of NAD to produce dihydroxyacetone.

* * * * *

SEQUENCE LISTING

<160> NUMBER OF SEQ ID NOS: 12

<210> SEQ ID NO 1
<211> LENGTH: 376
<212> TYPE: PRT
<213> ORGANISM: Pichia ofunaensis

<400> SEQUENCE: 1

```
Met Lys Gly Leu Leu Tyr Tyr Lys Thr Gly Asp Ile Arg Tyr Ser Glu
1               5                   10                  15

Asp Val Glu Glu Pro Glu Ile Leu Ser Ser His Asp Val Lys Ile Arg
            20                  25                  30

Val Lys Phe Cys Gly Ile Cys Gly Thr Asp Leu Lys Glu Tyr Thr Tyr
        35                  40                  45

Glu Gly Gly Pro Leu Phe Leu Pro Lys Pro Gly Ser Ser Asp Lys Ile
    50                  55                  60

Ser Gly Leu Glu Leu Pro Leu Cys Pro Gly His Glu Phe Cys Gly Val
65                  70                  75                  80

Val Glu Glu Val Gly Glu Ser Val Thr Arg Val Lys Pro Gly Asp Arg
                85                  90                  95

Val Ala Val Glu Ala Thr Thr His Cys Ser Asp Ala Val His Tyr Gly
            100                 105                 110

Val His Asp Met Glu Leu Cys Val Ala Cys Lys Asn Gly Ser Pro Asn
        115                 120                 125

Cys Cys Thr His Leu Ser Phe Cys Gly Leu Gly Gly Ala Ser Gly Gly
    130                 135                 140

Phe Ala Glu Lys Val Val Tyr Gly Glu Glu His Met Leu Lys Leu Pro
145                 150                 155                 160

Asp Ser Ile Pro Phe Asp Ile Gly Ala Leu Ile Glu Pro Leu Ala Val
                165                 170                 175

Ala Trp His Ala Val Glu Cys Ala Lys Phe Lys Pro Gly Ser Thr Ala
            180                 185                 190

Leu Val Leu Gly Gly Gly Pro Ile Gly Leu Ala Thr Ile Leu Ala Leu
        195                 200                 205

Gln Gly His Gln Ala Gly Arg Ile Val Cys Ser Glu Pro Ala Cys Ile
    210                 215                 220

Arg Arg Glu Tyr Ala Ala Lys Phe Gly Ala Glu Val Phe Asp Pro Ser
225                 230                 235                 240

Gln His Asp Asp Val Ile His Glu Leu Lys Ala Leu Leu Pro Glu Asn
                245                 250                 255
```

```
Gly Gly Phe Asp Ala Ser Phe Asp Cys Ser Gly Val Pro Gln Thr Phe
            260                 265                 270

Thr Thr Ser Ile Glu Ala Leu Ala Pro Gly Gly Met Ala Val Asn Val
            275                 280                 285

Ala Ile Trp Gly Asp His Ala Ile Asp Phe Gly Ala Met Cys Leu Thr
            290                 295                 300

Tyr Gln Glu Lys Thr Cys Thr Gly Ser Met Cys Tyr Thr Val Lys Asp
305                 310                 315                 320

Phe Glu Glu Val Ile Asn Ala Leu Asp Lys Gly Leu Ile Ser Ile Ser
                325                 330                 335

Lys Ala Arg Leu Met Ile Thr Gly Lys Val Asn Leu Lys Asp Gly Val
            340                 345                 350

Glu Leu Gly Phe Lys Gln Leu Ile Glu His Lys Glu Thr Asn Ile Lys
            355                 360                 365

Ile Leu Val Thr Pro Asp Glu Val
            370                 375

<210> SEQ ID NO 2
<211> LENGTH: 1131
<212> TYPE: DNA
<213> ORGANISM: Pichia ofunaensis

<400> SEQUENCE: 2 atgaaggat tgctctatta caagacagga gatatcagat actccgaaga cgttgaggag      60
cccgagatct tgagtagtca cgacgtcaag attcgggtaa aattctgcgg catttgtgga    120
actgacctta aggaatatac ttatgaagga ggtccattat tcttacctaa gcctggtagt    180
agcgacaaga tttctggggtt ggaattgccc ctctgtcctg acatgagtt ttgtggagtt    240 gtagaagaag ttggagaatc agtcactagg gtgaaacctg gtgatagagt tgcagtcgag    300
gctacgactc actgttcaga tgctgttcat tatggagttc atgatatgga attatgtgtt    360
gcgtgtaaaa atggaagtcc taactgctgc actcatttat ctttctgtgg attaggagga    420
gcaagcgggg gatttgctga aaagtagta tatggggagg aacatatgtt gaaacttcca    480
gactcaattc cgtttgatat tggtgccctt attgaaccat tagcagtggc ttggcatgca    540
gtggaatgcg cgaagtttaa accaggatcg actgcattag ttcttggtgg aggtccaatt    600
ggactggcta ccattctagc tctgcaagga catcaagcag acgcattgt atgttccgaa    660 cctgcttgta tcagacggga atatgccgcc aagtttggtg ctgaagtatt cgatccttca    720
cagcacgacg acgtcatcca tgaactcaaa gcattgcttc ctgagaatgg aggattcgat    780
gcatcatttg actgttcagg agttcctcag actttcacaa cttcaataga ggcactagca    840
cctggtggaa tggctgtcaa tgtagctatt tggggagatc atgctataga tttcggcgcc    900
atgtgtttga catatcaaga gaaaacctgt actggatcaa tgtgttacac agtaaaggac    960
tttgaagaag ttattaatgc ccttgataaa ggtctcatct ccatcagcaa agctcgtcta   1020
atgatcacag gcaaggttaa ccttaaagat ggagttgagc ttggatttaa gcaactgatc   1080
gaacataagg aaactaacat caagatcctt gttactcctg atgaagtgta g            1131

<210> SEQ ID NO 3
<211> LENGTH: 20
<212> TYPE: PRT
<213> ORGANISM: Pichia ofunaensis

<400> SEQUENCE: 3

Met Lys Gly Leu Leu Tyr Tyr Lys Thr Gly Asp Ile Arg Tyr Ser Glu
```

```
                1               5                   10                  15

Asp Val Glu Glu
            20

<210> SEQ ID NO 4
<211> LENGTH: 10
<212> TYPE: PRT
<213> ORGANISM: Pichia ofunaensis

<400> SEQUENCE: 4

Ile Leu Ser Ser His Asp Val Lys Ile Arg
1               5                   10

<210> SEQ ID NO 5
<211> LENGTH: 8
<212> TYPE: PRT
<213> ORGANISM: Pichia ofunaensis

<400> SEQUENCE: 5

Ala Thr Thr His Leu Ser Asp Ala
1               5

<210> SEQ ID NO 6
<211> LENGTH: 13
<212> TYPE: PRT
<213> ORGANISM: Pichia ofunaensis

<400> SEQUENCE: 6

Leu Lys Ala Leu Leu Pro Glu Asn Gly Gly Phe Asp Ala
1               5                   10

<210> SEQ ID NO 7
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 7 taytayaaara cnggngayat                                             20

<210> SEQ ID NO 8
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
```

-continued

```
<221> NAME/KEY: misc_feature
<222> LOCATION: (12)..(12)
<223> OTHER INFORMATION: n is a, c, g, or t

<400> SEQUENCE: 8
gcrtcraanc nccrttytc                                          20

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
atcaccaggt ttcaccctag tgac                                    24

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
ggaatgcgcg aagtttaaac cagg                                    24

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
ggaattctat aatgaaagga ttgctctatt                              30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
ggactagtct acacttcatc aggagtaaca                              30
```